(12) United States Patent
Levi et al.

(10) Patent No.: US 12,727,992 B2
(45) **Date of Patent: *Sep. 8, 2026**

(54) SEALING ELEMENT FOR PROSTHETIC HEART VALVE

(71) Applicant: EDWARDS LIFESCIENCES CORPORATION, Irvine, CA (US)

(72) Inventors: Tamir S. Levi, Zikhron Yaakov (IL); Giolnara Pinhas, Hadera (IL); Liraz Marom, Olesh (IL); Elena Sherman, Pardes Hana (IL); Noam Mizrahi, Irvine, CA (US); Delfin Rafael Ruiz, Sun Valley, CA (US); Sandip Vasant Pawar, Irvine, CA (US); Liron Tayeb, Peduel (IL)

(73) Assignee: Edwards Lifesciences Corporation, Irvine, CA (US)

( * ) Notice: Subject to any disclaimer, the term of this patent is extended or adjusted under 35 U.S.C. 154(b) by 119 days.

This patent is subject to a terminal disclaimer.

(21) Appl. No.: 18/195,808

(22) Filed: May 10, 2023

(65) Prior Publication Data

US 2023/0277306 A1 Sep. 7, 2023

Related U.S. Application Data

(60) Continuation of application No. 17/327,608, filed on May 21, 2021, now Pat. No. 12,551,336, which is a (Continued)

(51) Int. Cl.
*A61F 2/24* (2006.01)
*A61F 2/00* (2006.01)

(52) U.S. Cl.
CPC .......... *A61F 2/2415* (2013.01); *A61F 2/0077* (2013.01); *A61F 2/2409* (2013.01);

(Continued)

(58) Field of Classification Search
CPC .................. A61F 2/2409; A61F 2/2415; A61F 2250/0069
See application file for complete search history.

(56) References Cited

U.S. PATENT DOCUMENTS 3,365,728 A 1/1968 Miles et al.
3,564,617 A 2/1971 Sauvage et al.

(Continued)

FOREIGN PATENT DOCUMENTS

AU 2002212418 B2 5/2002
CA 2827556 A1 7/2012

(Continued)

OTHER PUBLICATIONS

Bonhoeffer P., et al., "Percutaneous Replacement of Pulmonary valve in a Right-Ventricle to Pulmonary-Artery Prosthetic Conduit with Valve Dysfunction," Early Report, The Lancet, Oct. 21, 2000, vol. 356, pp. 1403-1405.

(Continued)

*Primary Examiner* — Alvin J Stewart
(74) *Attorney, Agent, or Firm* — Klarquist Sparkman LLP

(57) ABSTRACT

An implantable prosthetic valve that is radially collapsible to a collapsed configuration and radially expandable to an expanded configuration includes an annular frame having an inflow end, an outflow end, and a longitudinal axis. A leaflet structure is positioned within the frame and secured thereto, and a sealing element is secured to the frame. The sealing element includes a first woven portion extending circumferentially around the frame. The first woven portion includes a plurality of interwoven filaments. The sealing element further includes a second woven portion extending circumferentially around the frame and spaced apart from the first (Continued)

woven portion along the longitudinal axis of the frame. At least a portion of the filaments comprise a hydrophilic surface treatment.

18 Claims, 22 Drawing Sheets

Related U.S. Application Data division of application No. 16/100,601, filed on Aug. 10, 2018, now Pat. No. 11,013,595.

(60) Provisional application No. 62/544,704, filed on Aug. 11, 2017.

(52) U.S. Cl.
CPC .... *A61F 2/2418* (2013.01); *A61F 2210/0076* (2013.01); *A61F 2230/0069* (2013.01); *A61F 2250/0069* (2013.01)

(56) References Cited

U.S. PATENT DOCUMENTS 3,725,961 A 4/1973 Magovern et al.
3,983,581 A 10/1976 Angell et al.
4,035,849 A 7/1977 Angell et al.
4,164,045 A 8/1979 Bokros et al.
4,490,859 A 1/1985 Black et al.
4,494,253 A * 1/1985 Bicer .................... A61F 2/2406 623/2.25
4,512,338 A 4/1985 Balko et al.
4,517,687 A 5/1985 Liebig et al.
4,695,280 A 9/1987 Watanabe et al.
4,743,250 A 5/1988 Kitagawa et al.
4,790,843 A 12/1988 Carpentier et al.
4,892,539 A 1/1990 Koch
5,059,177 A 10/1991 Towne et al.
5,178,630 A 1/1993 Schmitt
5,258,023 A 11/1993 Reger
5,403,305 A 4/1995 Sauter et al.
5,411,552 A 5/1995 Andersen et al.
5,443,500 A 8/1995 Sigwart
5,476,506 A 12/1995 Lunn
5,554,185 A 9/1996 Block et al.
5,628,786 A 5/1997 Banas et al.
5,693,088 A 12/1997 Lazarus
5,700,287 A 12/1997 Myers et al.
5,755,783 A 5/1998 Stobie et al.
5,769,882 A 6/1998 Fogarty et al.
5,776,188 A 7/1998 Shepherd et al.
5,843,161 A 12/1998 Solovay
5,843,179 A 12/1998 Vanney et al.
5,855,601 A 1/1999 Bessler et al.
5,957,949 A 9/1999 Leonhardt et al.
6,015,431 A 1/2000 Thornton et al.
6,110,198 A 8/2000 Fogarty et al.
6,120,534 A 9/2000 Ruiz
6,206,911 B1 3/2001 Milo
6,235,042 B1 5/2001 Katzman
6,270,527 B1 * 8/2001 Campbell ............ A61F 2/2412 623/2.18
6,306,141 B1 10/2001 Jervis
6,306,164 B1 10/2001 Kujawski
6,350,282 B1 * 2/2002 Eberhardt ............ A61F 2/2412 623/2.14
6,352,554 B2 3/2002 De Paulis
6,398,814 B1 6/2002 Paasimaa et al.
6,406,492 B1 6/2002 Lytle
6,409,758 B2 6/2002 Stobie et al.
6,419,696 B1 7/2002 Ortiz et al.
6,432,134 B1 8/2002 Anson et al.
6,482,228 B1 11/2002 Norred
6,527,979 B2 3/2003 Constantz et al.
6,540,782 B1 4/2003 Snyders
6,547,820 B1 * 4/2003 Staudenmeier ........ D04B 21/02 264/103
6,625,578 B2 9/2003 Spaur et al.
6,663,667 B2 12/2003 Dehdashtian et al.
6,729,356 B1 5/2004 Baker et al.
6,730,121 B2 5/2004 Ortiz et al.
6,773,456 B1 8/2004 Gordon et al.
6,783,554 B2 8/2004 Amara et al.
6,797,002 B2 9/2004 Spence et al.
6,814,754 B2 11/2004 Greenhalgh
6,846,325 B2 1/2005 Liddicoat
6,904,909 B2 6/2005 Andreas et al.
6,908,481 B2 6/2005 Cribier
6,911,040 B2 6/2005 Johnson et al.
6,971,998 B2 12/2005 Rosenman et al.
7,018,406 B2 3/2006 Seguin et al.
7,037,334 B1 5/2006 Hlavka et al.
7,077,861 B2 7/2006 Spence
7,101,395 B2 9/2006 Tremulis et al.
7,101,396 B2 9/2006 Artof et al.
7,125,421 B2 10/2006 Tremulis et al.
7,147,663 B1 12/2006 Berg et al.
7,166,126 B2 1/2007 Spence
7,166,127 B2 1/2007 Spence et al.
7,175,652 B2 2/2007 Cook et al.
7,192,441 B2 3/2007 Sherry
7,264,632 B2 9/2007 Wright et al.
7,404,824 B1 7/2008 Webler et al.
7,431,726 B2 10/2008 Spence et al.
7,445,632 B2 11/2008 McGuckin, Jr. et al.
7,452,371 B2 11/2008 Pavcnik et al.
7,524,331 B2 * 4/2009 Birdsall .................. A61L 27/34 623/2.11
7,527,646 B2 5/2009 Rahdert et al.
7,585,321 B2 * 9/2009 Cribier .................. A61F 2/2415 623/2.14
7,618,449 B2 11/2009 Tremulis et al.
7,637,946 B2 12/2009 Solem et al.
7,682,381 B2 3/2010 Rakos et al.
7,708,775 B2 5/2010 Rowe et al.
7,731,742 B2 6/2010 Schlick et al.
7,737,060 B2 6/2010 Strickler et al.
7,758,639 B2 7/2010 Mathis
7,780,725 B2 8/2010 Haug et al.
7,780,726 B2 8/2010 Seguin
7,785,366 B2 8/2010 Maurer et al.
7,921,678 B2 * 4/2011 Norris .................. D04B 21/205 66/195
7,942,927 B2 5/2011 Kaye et al.
7,951,195 B2 5/2011 Antonsson et al.
7,955,385 B2 6/2011 Crittenden
7,993,394 B2 * 8/2011 Hariton ................... B05B 1/185 623/2.17
8,016,882 B2 9/2011 Macoviak et al.
8,052,750 B2 11/2011 Tuval et al.
8,092,520 B2 1/2012 Quadri
8,105,377 B2 1/2012 Liddicoat
8,128,681 B2 3/2012 Shoemaker et al.
8,128,691 B2 3/2012 Keraenen
8,142,492 B2 3/2012 Forster et al.
8,236,049 B2 8/2012 Rowe et al.
8,323,335 B2 12/2012 Rowe et al.
8,377,115 B2 2/2013 Thompson
8,398,708 B2 3/2013 Meiri et al.
8,408,214 B2 * 4/2013 Spenser ................ A61F 2/2463 128/898
8,425,593 B2 4/2013 Braido et al.
8,430,925 B2 4/2013 Forster et al.
8,449,599 B2 5/2013 Chau et al.
8,449,605 B2 5/2013 Lichtenstein et al.
8,449,606 B2 5/2013 Eliasen et al.
8,641,757 B2 * 2/2014 Pintor ................... A61F 2/2409 623/2.11
8,657,872 B2 2/2014 Seguin
8,663,322 B2 3/2014 Keraenen
8,672,998 B2 3/2014 Lichtenstein et al.
8,685,086 B2 4/2014 Navia et al.
8,721,717 B2 5/2014 Shoemaker et al.

(56) References Cited

U.S. PATENT DOCUMENTS 8,795,352 B2 8/2014 O'Beirne et al.
8,795,357 B2 * 8/2014 Yohanan ............... A61F 2/2418 623/2.14
8,801,776 B2 8/2014 House et al.
8,808,356 B2 8/2014 Braido et al.
8,840,664 B2 9/2014 Karapetian et al.
8,845,721 B2 9/2014 Braido et al.
8,940,040 B2 * 1/2015 Shahriari ................. A61F 2/82 623/1.36
8,968,419 B2 3/2015 Calvez et al.
8,979,922 B2 3/2015 Jayasinghe et al.
8,986,373 B2 3/2015 Chau et al.
8,992,608 B2 3/2015 Haug et al.
9,078,747 B2 7/2015 Conklin
9,095,434 B2 8/2015 Rowe
9,119,718 B2 9/2015 Keränen
9,192,471 B2 11/2015 Bolling
9,220,594 B2 12/2015 Braido et al.
9,237,886 B2 1/2016 Seguin et al.
9,241,794 B2 1/2016 Braido et al.
9,289,296 B2 3/2016 Braido et al.
9,314,335 B2 4/2016 Konno
9,326,853 B2 5/2016 Olson et al.
9,326,856 B2 5/2016 Schraut et al.
9,345,571 B1 5/2016 Braido et al.
9,351,828 B2 5/2016 Braido et al.
9,351,831 B2 5/2016 Braido et al.
9,351,832 B2 5/2016 Braido et al.
9,393,110 B2 * 7/2016 Levi ...................... A61F 2/2433
9,414,911 B2 8/2016 Braido et al.
9,463,268 B2 10/2016 Spence
9,474,599 B2 10/2016 Keränen
9,526,572 B2 12/2016 Kunis
9,545,307 B2 1/2017 Braido et al.
9,549,815 B2 1/2017 Braido et al.
9,597,205 B2 3/2017 Tuval
9,597,430 B2 3/2017 Ratcliffe et al.
9,622,863 B2 4/2017 Karapetian et al.
9,655,389 B2 5/2017 Blakely
9,662,233 B2 5/2017 Tanahashi et al.
9,668,856 B2 6/2017 Para
9,820,852 B2 11/2017 Braido et al.
9,867,702 B2 1/2018 Keränen et al.
9,974,650 B2 * 5/2018 Nguyen-Thien-Nhon ................. A61F 2/2418
10,016,272 B2 7/2018 Spence et al.
10,016,276 B2 7/2018 Brunnett et al.
10,034,749 B2 7/2018 Spence et al.
10,039,637 B2 8/2018 Maimon et al.
10,052,198 B2 8/2018 Chau et al.
10,195,028 B2 2/2019 Hosmer et al.
10,195,033 B2 2/2019 Tuval et al.
10,226,339 B2 3/2019 Spence et al.
10,357,361 B2 7/2019 Rafi et al.
10,463,479 B2 11/2019 Manash et al.
10,687,938 B2 6/2020 Patel et al.
10,828,150 B2 11/2020 Tamir
11,013,595 B2 * 5/2021 Levi ...................... A61F 2/2415
11,020,225 B2 6/2021 Keränen et al.
11,039,924 B2 6/2021 Yaron
11,045,312 B2 * 6/2021 Flaction .................... A61F 2/06
11,065,111 B2 7/2021 Manash et al.
11,141,273 B2 10/2021 Dakin et al.
11,185,406 B2 11/2021 Haivatov et al.
11,364,114 B2 6/2022 Gorman, III et al.
11,382,748 B2 7/2022 Keränen et al.
11,471,282 B2 10/2022 Argento et al.
11,547,563 B2 1/2023 Keränen et al.
11,654,025 B2 5/2023 O'Carroll et al.
11,666,441 B2 6/2023 Mcdaniel et al.
11,744,702 B1 9/2023 Shahriari et al.
11,883,281 B2 * 1/2024 Hoang .................. A61F 2/2409
12,064,341 B2 * 8/2024 Hoang .................. A61F 2/2418
12,102,521 B1 10/2024 Koch
2001/0021872 A1 9/2001 Bailey et al.
2001/0027338 A1 10/2001 Greenberg
2001/0039450 A1 11/2001 Pavcnik et al.
2002/0032481 A1 3/2002 Gabbay
2002/0045936 A1 4/2002 Moe
2002/0099441 A1 7/2002 Dehdashtian
2002/0107535 A1 8/2002 Wei et al.
2002/0151958 A1 10/2002 Chuter
2002/0151970 A1 10/2002 Garrison et al.
2002/0173841 A1 11/2002 Ortiz et al.
2003/0040809 A1 2/2003 Goldmann et al.
2003/0074058 A1 4/2003 Sherry
2003/0109923 A1 * 6/2003 Chinn .................. A61F 2/2412 623/2.4
2003/0120332 A1 6/2003 Hartley
2003/0167089 A1 9/2003 Lane
2003/0225420 A1 12/2003 Wardle
2003/0236567 A1 12/2003 Elliot
2004/0033364 A1 2/2004 Spiridigliozzi et al.
2004/0044397 A1 3/2004 Stinson
2004/0082989 A1 4/2004 Cook et al.
2004/0098096 A1 5/2004 Eton
2004/0111006 A1 6/2004 Alferness et al.
2004/0167620 A1 8/2004 Ortiz et al.
2004/0210304 A1 10/2004 Seguin et al.
2004/0210305 A1 * 10/2004 Shu ...................... A61F 2/2412 623/2.11
2004/0219854 A1 11/2004 Groitzsch et al.
2004/0225353 A1 11/2004 McGuckin et al.
2004/0260389 A1 12/2004 Case et al.
2005/0043790 A1 2/2005 Seguin
2005/0045566 A1 3/2005 Larkin et al.
2005/0070930 A1 3/2005 Kammerer
2005/0119682 A1 6/2005 Nguyen et al.
2005/0119735 A1 6/2005 Spence et al.
2005/0137687 A1 6/2005 Salahieh et al.
2005/0137691 A1 6/2005 Salahieh et al.
2005/0182486 A1 8/2005 Gabbay
2005/0203614 A1 9/2005 Forster et al.
2005/0273155 A1 12/2005 Bahler et al.
2006/0004442 A1 * 1/2006 Spenser ................ A61F 2/2472 623/1.21
2006/0085063 A1 4/2006 Shastri et al.
2006/0195134 A1 8/2006 Crittenden
2006/0265056 A1 11/2006 Nguyen et al.
2006/0271172 A1 11/2006 Tehrani
2007/0032805 A1 2/2007 Therin et al.
2007/0073387 A1 3/2007 Forster et al.
2007/0118210 A1 5/2007 Pinchuk
2007/0185572 A1 8/2007 Solem et al.
2007/0203575 A1 8/2007 Forster et al.
2007/0213813 A1 9/2007 Von Segesser et al.
2007/0232898 A1 10/2007 Huynh et al.
2007/0239265 A1 10/2007 Birdsall
2007/0244553 A1 10/2007 Rafiee et al.
2007/0244569 A1 10/2007 Weber et al.
2007/0255400 A1 * 11/2007 Parravicini ........... A61F 2/2409 623/2.14
2007/0265700 A1 11/2007 Eliasen et al.
2007/0293808 A1 12/2007 Williams et al.
2008/0004697 A1 1/2008 Lichtenstein et al.
2008/0033542 A1 2/2008 Antonsson et al.
2008/0077235 A1 3/2008 Kirson
2008/0140190 A1 6/2008 Macoviak et al.
2008/0147171 A1 6/2008 Ashton et al.
2008/0208327 A1 8/2008 Rowe
2008/0208330 A1 8/2008 Keranen
2008/0228265 A1 9/2008 Spence et al.
2008/0243245 A1 10/2008 Thambar et al.
2008/0275503 A1 11/2008 Spence et al.
2009/0099653 A1 4/2009 Suri et al.
2009/0132035 A1 5/2009 Roth et al.
2009/0171443 A1 7/2009 Kuppurathanam et al.
2009/0177278 A1 7/2009 Spence
2009/0192601 A1 7/2009 Rafiee et al.
2009/0234318 A1 9/2009 Loulmet et al.
2009/0259307 A1 10/2009 Gross et al.
2009/0276038 A1 11/2009 Tremulis et al.
2009/0276040 A1 11/2009 Rowe et al.
2009/0299471 A1 12/2009 Keraenen

(56) References Cited

U.S. PATENT DOCUMENTS

2009/0319037 A1 12/2009 Rowe et al.
2010/0016872 A1 1/2010 Bayon et al.
2010/0036484 A1 2/2010 Hariton et al.
2010/0076549 A1 3/2010 Keidar et al.
2010/0145440 A1 6/2010 Keraenen
2010/0152839 A1 6/2010 Shandas et al.
2010/0161047 A1 6/2010 Cabiri
2010/0168839 A1 7/2010 Braido et al.
2010/0217382 A1 8/2010 Chau et al.
2010/0256751 A1 10/2010 Rowe et al.
2010/0312333 A1 12/2010 Navia et al.
2010/0318183 A1 12/2010 Keraenen
2010/0318184 A1 12/2010 Spence
2010/0331971 A1 12/2010 Keraenen et al.
2010/0331973 A1 12/2010 Keraenen
2011/0029072 A1 2/2011 Gabbay
2011/0098802 A1* 4/2011 Braido .................. A61F 2/2466 623/2.11
2011/0106247 A1 5/2011 Miller et al.
2011/0137397 A1 6/2011 Chau et al.
2011/0178597 A9 7/2011 Navia et al.
2011/0208298 A1 8/2011 Tuval et al.
2011/0218621 A1 9/2011 Antonsson et al.
2011/0224785 A1 9/2011 Hacohen
2011/0245911 A1 10/2011 Quill et al.
2011/0288634 A1 11/2011 Tuval et al.
2011/0295361 A1 12/2011 Claiborne, III et al.
2011/0319989 A1 12/2011 Lane et al.
2011/0319990 A1 12/2011 Macoviak et al.
2012/0016464 A1 1/2012 Seguin
2012/0035719 A1 2/2012 Forster et al.
2012/0053680 A1 3/2012 Bolling et al.
2012/0059458 A1 3/2012 Buchbinder et al.
2012/0150287 A1 6/2012 Forster et al.
2012/0172981 A1* 7/2012 DuMontelle .......... A61F 2/2412 623/2.17
2012/0215303 A1 8/2012 Quadri et al.
2012/0283820 A1 11/2012 Tseng et al.
2012/0310328 A1 12/2012 Olson et al.
2012/0316643 A1 12/2012 Keraenen
2013/0006352 A1 1/2013 Yaron
2013/0150957 A1* 6/2013 Weber ..................... A61L 31/10 623/2.15
2013/0190682 A1 7/2013 Bonutti et al.
2013/0190865 A1 7/2013 Anderson
2013/0197622 A1* 8/2013 Mitra .................... A61F 2/2418 623/1.15
2013/0204234 A1 8/2013 Cully et al.
2013/0204311 A1 8/2013 Kunis
2013/0260104 A1 10/2013 Dua et al.
2013/0310917 A1 11/2013 Richter et al.
2013/0310928 A1 11/2013 Morriss et al.
2013/0331929 A1* 12/2013 Mitra .................... A61F 2/2418 623/2.11
2013/0338765 A1 12/2013 Braido et al.
2014/0074299 A1 3/2014 Endou et al.
2014/0081394 A1 3/2014 Keraenen et al.
2014/0155997 A1* 6/2014 Braido .................. A61F 2/2409 623/2.37
2014/0163669 A1 6/2014 Ben-Zvi et al.
2014/0172070 A1 6/2014 Seguin
2014/0236287 A1 8/2014 Clague et al.
2014/0243966 A1* 8/2014 Garde ................... A61F 2/2418 623/2.18
2014/0277417 A1* 9/2014 Schraut ................. A61F 2/2418 623/2.17
2014/0277428 A1* 9/2014 Skemp .................. A61F 2/2418 623/2.42
2014/0350663 A1 11/2014 Braido et al.
2014/0358222 A1 12/2014 Gorman, III et al.
2014/0379074 A1 12/2014 Spence et al.
2015/0025623 A1 1/2015 Granada et al.
2015/0073541 A1 3/2015 Salahieh et al.
2015/0073546 A1 3/2015 Braido
2015/0122687 A1* 5/2015 Zeng ...................... A61B 50/30 53/467
2015/0148896 A1 5/2015 Karapetian et al.
2015/0157455 A1 6/2015 Hoang et al.
2015/0173898 A1 6/2015 Drasler et al.
2015/0190227 A1 7/2015 Johnson et al.
2015/0216658 A1* 8/2015 Braido .................. A61F 2/2433 623/2.13
2015/0230921 A1 8/2015 Chau et al.
2015/0245910 A1 9/2015 Righini et al.
2015/0282931 A1 10/2015 Brunnett et al.
2015/0282932 A1 10/2015 Neuman et al.
2015/0305860 A1 10/2015 Wang et al.
2015/0335421 A1* 11/2015 Figulla .................. A61F 2/2418 623/2.17
2015/0335428 A1 11/2015 Keränen
2015/0335430 A1 11/2015 Loulmet et al.
2015/0366664 A1* 12/2015 Guttenberg ........... A61F 2/2418 623/2.17
2015/0374493 A1 12/2015 Yaron et al.
2016/0015514 A1 1/2016 Lashinski et al.
2016/0030165 A1* 2/2016 Mitra .................... A61F 2/0095 206/438
2016/0074165 A1 3/2016 Spence et al.
2016/0095705 A1 4/2016 Keränen et al.
2016/0143732 A1* 5/2016 Glimsdale ............. A61F 2/2418 29/525.09
2016/0184095 A1 6/2016 Spence et al.
2016/0199177 A1 7/2016 Spence et al.
2016/0213466 A1 7/2016 Braido et al.
2016/0213468 A1 7/2016 Braido et al.
2016/0242904 A1 8/2016 Braido et al.
2016/0256276 A1 9/2016 Yaron
2016/0317305 A1* 11/2016 Pelled ................... A61F 2/2412
2016/0346080 A1 12/2016 Righini et al.
2016/0354201 A1* 12/2016 Keogh .................. A61F 2/2418
2016/0361160 A1* 12/2016 Braido .................. A61F 2/2418
2017/0000604 A1* 1/2017 Conklin ................ A61F 2/2418
2017/0007399 A1 1/2017 Keränen
2017/0007402 A1 1/2017 Zerkowski et al.
2017/0056163 A1* 3/2017 Tayeb ................... A61F 2/2409
2017/0056164 A1* 3/2017 Wang ...................... A61F 2/844
2017/0065411 A1* 3/2017 Grundeman .......... A61F 2/2415
2017/0172736 A1 6/2017 Chadha et al.
2017/0217385 A1 8/2017 Rinkleff et al.
2017/0266005 A1 9/2017 McGuckin, Jr.
2017/0273784 A1 9/2017 Racchini et al.
2017/0273789 A1 9/2017 Yaron et al.
2017/0281337 A1 10/2017 Campbell
2017/0360426 A1 12/2017 Hacohen et al.
2018/0000580 A1 1/2018 Wallace et al.
2018/0028310 A1 2/2018 Gurovich et al.
2018/0085217 A1 3/2018 Lashinski et al.
2018/0110609 A1 4/2018 Ehnes et al.
2018/0133003 A1* 5/2018 Levi ...................... A61F 2/2412
2018/0168804 A1* 6/2018 Nguyen ................ A61F 2/2409
2018/0206074 A1 7/2018 Tanasa et al.
2018/0289481 A1 10/2018 Dolan
2018/0303606 A1 10/2018 Rothstein et al.
2018/0318073 A1 11/2018 Tseng et al.
2018/0318080 A1 11/2018 Quill et al.
2019/0069995 A1* 3/2019 Levi ...................... A61F 2/2418
2019/0365530 A1* 12/2019 Hoang .................. A61F 2/2409
2020/0054453 A1 2/2020 Zerkowski et al.
2020/0060814 A1* 2/2020 Murphy ................ A61F 2/2475
2020/0360143 A1 11/2020 O'Carroll et al.
2021/0068947 A1* 3/2021 Nash ....................... A61L 27/18
2021/0212826 A1 7/2021 Zerkowski et al.
2021/0275296 A1* 9/2021 Levi ....................... D03D 27/04
2021/0353408 A1* 11/2021 Chen ..................... A61F 2/2418
2021/0361426 A1 11/2021 Hacohen
2022/0039945 A1* 2/2022 Guttenberg ........... A61F 2/2472
2022/0338979 A1* 10/2022 Benichou .............. A61F 2/2409
2022/0370193 A1* 11/2022 Pouletty ............. A61B 17/1214
2023/0017301 A1* 1/2023 Sherman ............... A61F 2/2418
2023/0086853 A1 3/2023 Zerkowski et al.
2023/0172708 A1* 6/2023 Heniford ............... A61F 2/2415 623/1.15
2023/0263625 A1 8/2023 Heniford et al.

(56) References Cited

U.S. PATENT DOCUMENTS

| | | | |
|---|---|---|---|
| 2023/0277312 A1 | 9/2023 | Nguyen et al. | |
| 2023/0372093 A1 | 11/2023 | Bukin et al. | |
| 2023/0414348 A1* | 12/2023 | Maimon | A61F 2/2418 |
| 2024/0033079 A1* | 2/2024 | Zamani | A61F 2/2415 |
| 2024/0081988 A1* | 3/2024 | Desai | D01F 6/92 |
| 2024/0366371 A1 | 11/2024 | Bukin et al. | |
| 2025/0064609 A1 | 2/2025 | Flanagan et al. | |
| 2025/0090311 A1 | 3/2025 | Gurovich et al. | |

FOREIGN PATENT DOCUMENTS

| | | | |
|---|---|---|---|
| CN | 1684644 | A | 10/2005 |
| CN | 1714766 | A | 1/2006 |
| CN | 101588771 | A | 11/2009 |
| DE | 19532846 | A1 | 3/1997 |
| DE | 19907646 | A1 | 8/2000 |
| EP | 0592410 | B1 | 10/1995 |
| EP | 1432369 | A1 | 6/2004 |
| EP | 1521550 | A2 | 4/2005 |
| EP | 1296618 | B1 | 1/2008 |
| EP | 2155114 | A1 | 2/2010 |
| EP | 1827314 | B1 | 12/2010 |
| EP | 2299938 | A2 | 3/2011 |
| EP | 2520250 | A1 | 11/2012 |
| EP | 2572675 | A3 | 3/2013 |
| EP | 2572676 | A3 | 3/2013 |
| EP | 2698129 | A1 | 2/2014 |
| EP | 2745805 | A1 | 6/2014 |
| EP | 2749254 | A1 | 7/2014 |
| EP | 2815723 | A1 | 12/2014 |
| EP | 2815725 | A1 | 12/2014 |
| EP | 2967851 | A2 | 1/2016 |
| EP | 2926766 | B1 | 2/2016 |
| EP | 2815724 | B1 | 6/2016 |
| EP | 3028670 | A1 | 6/2016 |
| EP | 3028671 | A1 | 6/2016 |
| EP | 3025680 | B1 | 2/2017 |
| EP | 3025681 | B1 | 2/2017 |
| EP | 3395296 | B1 | 12/2019 |
| EP | 2072027 | B1 | 6/2020 |
| EP | 2747708 | B1 | 1/2022 |
| GB | 2222954 | A | 3/1990 |
| JP | H04226647 | A | 8/1992 |
| WO | 1997048350 | A1 | 12/1997 |
| WO | 1998029057 | A1 | 7/1998 |
| WO | 2000044313 | A1 | 8/2000 |
| WO | 2001006959 | A1 | 2/2001 |
| WO | WO-2001054625 | A1 | 8/2001 |
| WO | 2002019951 | A1 | 3/2002 |
| WO | 2002036048 | A1 | 5/2002 |
| WO | WO-2002047575 | A2 | 6/2002 |
| WO | 2003003949 | A3 | 1/2003 |
| WO | 2003037222 | A3 | 5/2003 |
| WO | 2003047468 | A1 | 6/2003 |
| WO | 2003088873 | A1 | 10/2003 |
| WO | 2003096932 | A1 | 11/2003 |
| WO | WO-2005102015 | A2 | 11/2005 |
| WO | 2006005015 | A2 | 1/2006 |
| WO | WO-2006011127 | A2 | 2/2006 |
| WO | WO-2007067942 | A1 | 6/2007 |
| WO | 2009042196 | A2 | 4/2009 |
| WO | WO-2009080801 | A1 | 7/2009 |
| WO | WO-2009134701 | A2 | 11/2009 |
| WO | WO-2010057262 | A1 | 5/2010 |
| WO | WO-2010121076 | A2 | 10/2010 |
| WO | WO-2012063228 | A1 | 5/2012 |
| WO | WO-2013028387 | A2 | 2/2013 |
| WO | WO-2013110722 | A2 | 8/2013 |
| WO | WO-2013114214 | A2 | 8/2013 |
| WO | WO-2015023579 | A1 | 2/2015 |
| WO | WO-2015023862 | A2 | 2/2015 |
| WO | WO-2015124631 | A2 | 8/2015 |
| WO | WO-2015152980 | A1 | 10/2015 |
| WO | WO-2015198125 | A1 | 12/2015 |
| WO | WO-2016038017 | A1 | 3/2016 |
| WO | WO-2016130820 | A1 | 8/2016 |
| WO | 2017099820 | A3 | 6/2017 |
| WO | WO-2017103833 | A1 | 6/2017 |
| WO | WO-2017125170 | A1 | 7/2017 |
| WO | WO-2017139460 | A1 | 8/2017 |
| WO | WO-2018039589 | A1 | 3/2018 |
| WO | WO-2018112429 | A1 | 6/2018 |

OTHER PUBLICATIONS

Casselman F., et al., "Reducing Operative Mortality in Valvular Reoperations: The "Valve in Ring" Procedure," Brief Technique Reports, The Journal of Thoracic and Cardiovascular Surgery, May 2011, vol. 141, No. 5, pp. 1317-1318.

Cheung A., et al., "Live Case Transmissions," Structural, Case Summary, Nyha III CHF, St. Paul's Hospital/University of British Columbia, Sep. 23, 2010, 6 Pages.

Cheung A., et al., "Transapical T ranscatheter Mitral Valve-in-Valve Implantation in a Human," The Annals of Thoracic Surgery: The Society of Thoracic Surgeons, 2009, vol. 87, pp. e18-e20.

De Weger A., et al., "First-in-Man Implantation of a Trans-Catheter Aortic Valve in a Mitral Annuloplasty Ring: Novel Treatment Modality for Failed Mitral Valve Repair," European Journal of Cardio-Thoracic Surgery, 2011, vol. 39, pp. 1054-1056.

Descoutures F., et al., "Transcatheter Valve-in-Ring Implantation After Failure of Surgical Mitral Repair," European Journal of Cardio-Thoracic Surgery, 2013, vol. 44, pp. e8-e15.

Himbert D., et aL, "Transseptal Implantation of a Transcatheter Heart Valve in a Mitral Annuloplasty Ring to Treat Mitral Repair Failure," Circulation Cardiovascular Interventions, American Heart Association, Aug. 2011, pp. 396-398 (5 Pages).

Himbert D., et aL, "Transvenous Mitral Valve Repair Replacement After Failure of Surgical Ring Annuloplasty," Research Correspondence, Journal of the American College of Cardiology, Sep. 25, 2012, vol. 60, No. 13, pp. 1205-1206.

Kempfert J., etal., "Minimally Invasive Off-Pump Valve-in-a-Ring implantation: The Atria! Transcatheter Approach for Re-Operative Mitral Valve Replacement After Failed Repair," European Journal of Cardio-Thoracic Surgery, 2009, vol. 35, pp. 965-969.

Ma L., et aL, "Double-crowned Valved Stents for Off-pump Mitral Valve Replacement," European Journal of Cardio-thoracic Surgery, 2005, vol. 28, No. 2, pp. 194-199, Discussion 198-9, (Aug. 2008).

Shuto T., etal., "Percutaneous Transvenous Melody Valve-in-Ring Procedure for Mitral Valve Replacement," Journal of the American College of Cardiology, Dec. 6, 2011, vol. 58, No. 24, pp. 2475-2480.

Walther T., et al., "Valve-in-a-Valve Concept for Transcatheter Minimally Invasive Repeat Xenograph Implantation," Preclinical Studies, Journal of the American College of Cardiology, Jul. 3, 2007, vol. 50, No. 1, pp. 56-60.

Walther T., etal., "Human Minimally Invasive Off-Pump Valve-in-a-Valve Implantation," Case Reports, The Society of Thoracic Surgeons, The Annals of Thoracic Surgery, 2008, vol. 85, pp. 1072-1073.

Walther T., etaL, "Trans-catheter Valve-in-valve Implantation: In Vitro Hydrodynamic Performance of the SAPIEN + Cloth Trans-Catheter Heart Valve in the Carpentier-Edwards Perimount Valves," European Journal of Cardio-Thoracic Surgery, 2011, vol. 40, pp. 1 120-1126, (Sep. 23, 2010).

Webb J., et al., "Mitral Valve in Valve," TCT Sep. 2009, Live Case: 30 Minutes, St. Paul's Hospital/University of British Columbia, Sep. 23, 2009, 14 Pages.

Webb J.G., et al., "Transcatheter Valve-in-Valve Implantation for Failed Bioprosthetic Heart Valves," Journal of the American Heart Association, Apr. 27, 2010, vol. 121, pp. 1848-1857 (11 Pages).

Wenaweser P., et al., "Percutaneous Aortic Valve Replacement for Severe Aortic Regurgitation in Degenerated Bioprosthesis: The First Valve Procedure Using Corevalve Revalving System," Catheterization and Cardiovascular Interventions, 2007, vol. 70, pp. 760-764.

* cited by examiner 220
228B
226C
226B
228A
226A 202
204
212
L
204A
204B
204C

208
A
B
205
216
220
218
206
V
IV
III
II
I 212, 224
232
230

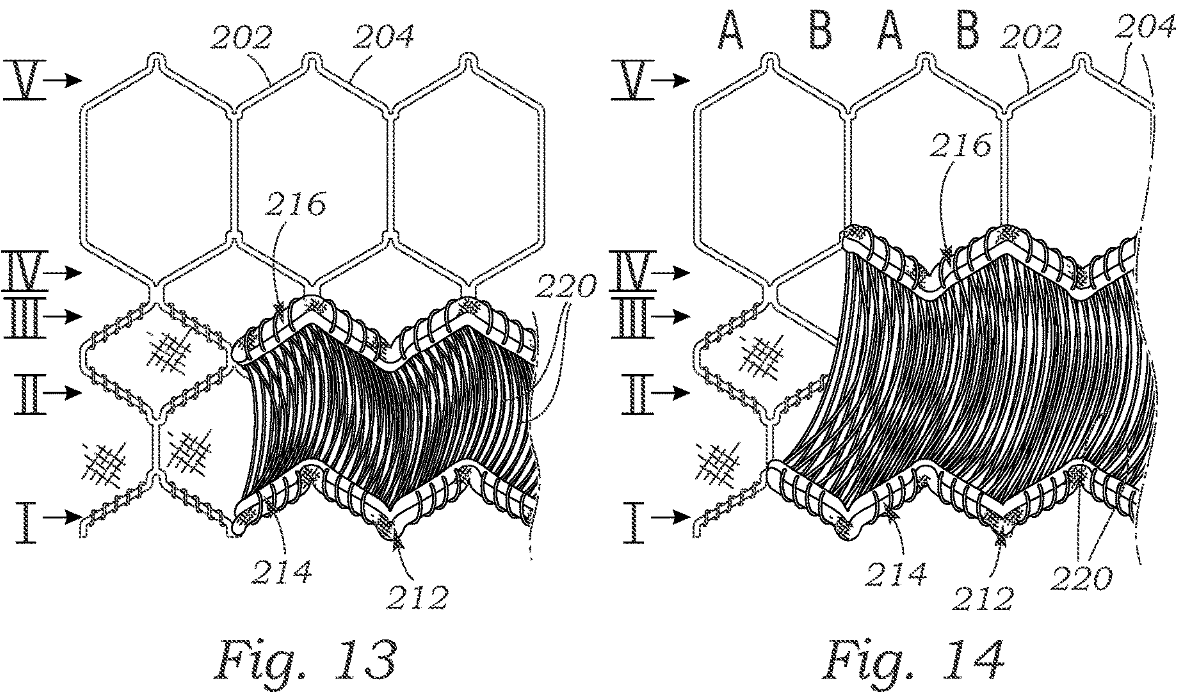
Fig. 13
Fig. 14
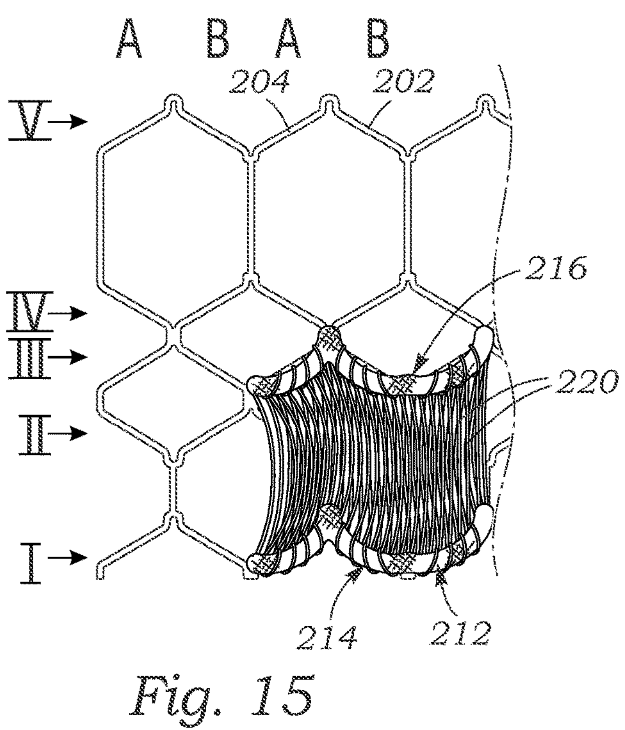
Fig. 15

W5
x
y
1006C
1014
1004C
1010,
1012
1006B
1004B
1006A

W4
x
y
1006C
1014
1004C
1010,
1012
1006B
1014
1004B
1006A

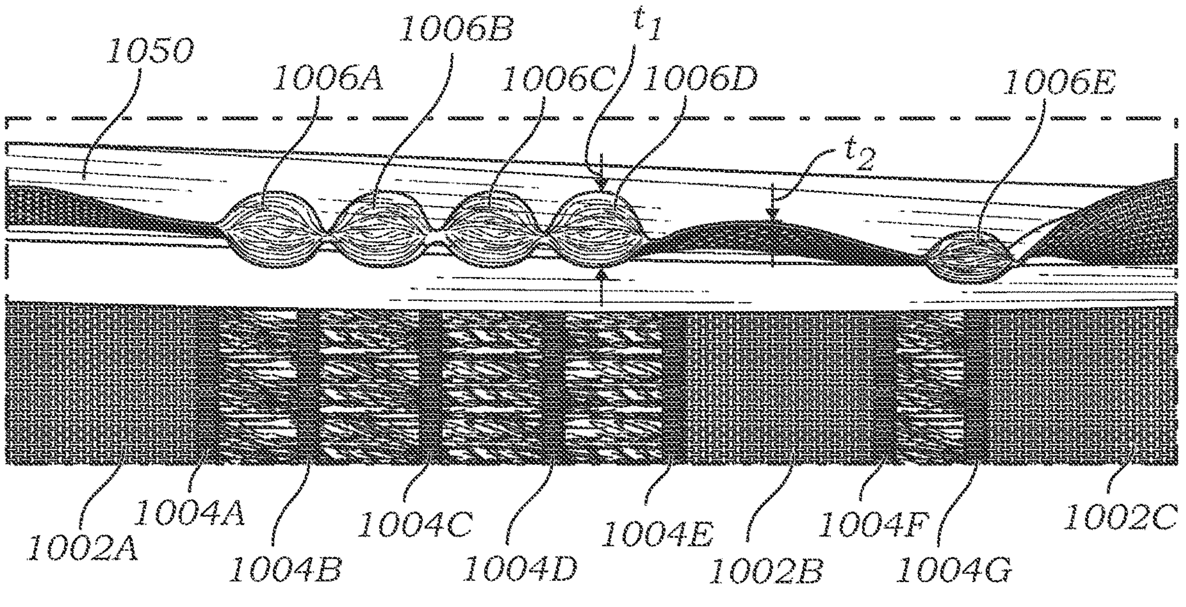
*Fig. 38*
1060
1064
1062
*Fig. 39A*
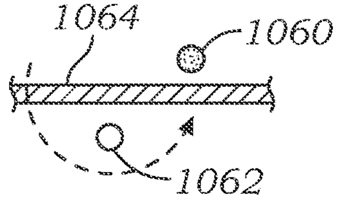
*Fig. 39B*

SEALING ELEMENT FOR PROSTHETIC HEART VALVE

CROSS REFERENCE TO RELATED APPLICATION

The present application is a continuation of U.S. patent application Ser. No. 17/327,608, filed May 21, 2021, which is a divisional of U.S. patent application Ser. No. 16/100,601, filed Aug. 10, 2018, issued as U.S. Pat. No. 11,013,595, which claims priority to and the benefit of U.S. Provisional Application No. 62/544,704, filed on Aug. 11, 2017. Each of the foregoing applications is incorporated herein by reference in their entirety.

FIELD

The present application relates to embodiments of sealing elements for prosthetic heart valves and methods of making the same.

BACKGROUND

The heart can suffer from various valvular diseases or malformations that result in significant malfunctioning of the heart, and ultimately require replacement of the native heart valve with an artificial valve. Procedures in which radially collapsible transcatheter heart valves are percutaneously introduced in a compressed state on a catheter and expanded at the treatment location are gaining popularity, especially among patient populations for whom traditional surgical procedures pose a high risk of morbidity or mortality.

It can be important to reduce or prevent blood leakage past the prosthetic valve after implantation. Thus, transcatheter heart valves often include a sealing element such as a paravalvular leakage skirt to reduce the amount of leakage past the prosthetic valve. However, differences between the diameter of the prosthetic valve and the native annulus into which the valve is implanted, along with features of a particular patient's anatomy such as calcification, tissue prominences, recesses, folds, and the like, can make it difficult to achieve a seal between the prosthetic valve and the native annulus. Accordingly, there is a need for improved paravalvular sealing elements for prosthetic heart valves.

SUMMARY

Certain embodiments of the disclosure concern prosthetic valves including various embodiments of sealing elements. In a representative embodiment, an implantable prosthetic valve that is radially collapsible to a collapsed configuration and radially expandable to an expanded configuration comprises an annular frame having an inflow end, an outflow end, and a longitudinal axis. A leaflet structure is positioned within the frame and secured thereto, and a sealing element is secured to the frame. The sealing element comprises a first woven portion extending circumferentially around the frame. The first woven portion comprises a plurality of interwoven filaments. The sealing element further comprises a second woven portion extending circumferentially around the frame and spaced apart from the first woven portion along the longitudinal axis of the frame. At least a portion of the filaments exit the weave of the first woven portion and form loops extending radially outwardly from the frame.

In some embodiments, the filaments that form the loops extend from and return to the first woven portion.

In some embodiments, the first woven portion comprises a first row of loops, and the second woven portion comprises a second row of loops. The loops of the second row of loops can comprise filaments that extend from and return to the second woven portion.

In some embodiment, the loops of the second row of loops are circumferentially offset from the loops of the first row of loops.

In some embodiments, the plurality of interwoven filaments of the first woven portion further comprises at least one first filament interwoven with a plurality of second filaments, and a portion of the at least one first filament forms the loops of the first woven portion.

In some embodiments, the sealing element further comprises an intermediate sealing portion between the first and second woven portions. The intermediate sealing portion comprises a plurality of second filaments, and a portion of the at least one first filament extends along the longitudinal axis of the frame between the first woven portion and the second woven portion, and is interwoven with the second filaments of the intermediate sealing portion.

In some embodiments, a portion of the at least one first filament forms the loops of the second woven portion.

In some embodiments, the second filaments are warp yarns and the at least one first filament is a weft yarn.

In some embodiments, at least one of the warp and weft yarns comprise textured yarns.

In some embodiments, the warp and weft yarns comprise fibers having a diameter of from 1 μm to 20 μm to promote thrombus formation around the sealing element.

In some embodiments, the filaments that form the loops originate from the first woven portion and extend curvilinearly along the longitudinal axis of the frame to the second woven portion.

In some embodiments, the filaments that form the loops exit a weave of the first woven portion and are incorporated into a weave of the second woven portion such that the loops form a floating yarn portion between the first and second woven portions.

In some embodiments, the floating yarn portion comprises a first layer of loops and a second layer of loops radially outward of the first layer of loops.

In some embodiments, the sealing element comprises a first fabric strip, a second fabric strip, and a third fabric strip. A plurality of the filaments that form the loops extend between the first fabric strip and the second fabric strip, and a plurality of the filaments that form the loops extend between the second fabric strip and the third fabric strip. The sealing element is folded about the second fabric strip such that the first fabric strip and the third fabric strip are adjacent each other to form the first woven portion, the filaments extending between the first fabric strip and the second fabric strip form the first layer of loops, and the filaments extending between the second fabric strip and the third fabric strip form the second layer of loops.

In some embodiments, the sealing element is secured to the frame such that the filaments that exit the weave of the first woven portion form the loops when the frame is in the expanded configuration, and are pulled straight when the frame is in the collapsed configuration.

In another representative embodiment, a method comprises mounting any of the prosthetic valves herein to a distal end portion of a delivery apparatus, advancing the delivery apparatus through a patient's vasculature to the heart, and expanding the prosthetic valve in a native heart valve of the heart such that the prosthetic valve regulates blood flow through the native heart valve.

In another representative embodiment, a method of making a sealing element for a prosthetic heart valve comprises weaving at least one weft yarn together with a plurality of warp yarns to form a first woven portion, dropping the at least one weft yarn from a weave of the first woven portion, and looping the at least one weft yarn around a removable warp yarn. The removable warp yarn is spaced apart from the first woven portion, and the at least one weft yarn is looped around the removable warp yarn such that the at least one weft yarn extends over, and is not interwoven with, warp yarns disposed between the first woven portion and the removable warp yarn. The method further comprises reincorporating the at least one weft yarn into the weave of the first woven portion such that the at least one weft yarn forms a loop that extends from and returns to the first woven portion, and removing the removable warp yarn from the sealing element to release the loop formed by the at least one weft yarn.

In some embodiments, before removing the removable warp yarn, the method further comprises repeating the weaving, the dropping, the looping, and the reincorporating to form a plurality of loops about a circumference of the sealing element.

In some embodiments, the method further comprises shape-setting the plurality of loops such that the loops extend outwardly from the sealing element.

In some embodiments, the method further comprises before removing the removable warp yarn, weaving the at least one weft yarn together with warp yarns such that the at least one weft yarn extends beyond the removable warp yarn and forms a second woven portion spaced apart from the first woven portion. The method further comprises dropping the at least one weft yarn from a weave of the second woven portion, and looping the at least one weft yarn around a second removable warp yarn that is spaced apart from the second woven portion. The at least one weft yarn can be looped around the second removable warp yarn such that the at least one weft yarn extends over, and is not interwoven with, warp yarns disposed between the second woven portion and the second removable warp yarn. The method can further comprise reincorporating the at least one weft yarn into the weave of the second woven portion such that the at least one weft yarn forms a second loop that extends from and returns to the second woven portion.

The foregoing and other objects, features, and advantages of the disclosed technology will become more apparent from the following detailed description, which proceeds with reference to the accompanying figures.

BRIEF DESCRIPTION OF THE DRAWINGS

FIG. 13 is a side elevation view illustrating a portion of the frame of the prosthetic valve of FIG. 9 with the first woven portion of the paravalvular leakage seal coupled to a first rung of frame struts, and the second woven portion coupled to a third rung of frame struts.

FIG. 14 is a side elevation view illustrating a portion of the frame of the prosthetic valve of FIG. 9 with the first woven portion of the paravalvular leakage seal coupled to a first rung of frame struts, and the second woven portion coupled to a fourth rung of frame struts.

FIG. 15 is a side elevation view illustrating a portion of the frame of the prosthetic valve of FIG. 9 with the paravalvular leakage seal draped along the struts of the frame.

FIG. 38 is a perspective view illustrating an edge portion of the sealing member of FIG. 32.

FIGS. 39A-39J illustrate various examples of leno weave patterns and leno weaving techniques.

DETAILED DESCRIPTION

The present disclosure concerns embodiments of sealing elements for implantable prosthetic devices, such as prosthetic heart valves. The present inventors surprisingly have discovered that effective sealing can be accomplished by sealing elements including a plurality of filaments, such as yarns and/or fibers, that extend from the sealing element and are configured to prompt a biological response at the cellular level to promote thrombogenesis around the sealing element.

For example, the sealing elements described herein can be configured as fabric skirts including woven portions from which filaments or yarns extend, and which can contact and/or conform to the surrounding anatomy to enhance the sealing properties of the skirt. In certain configurations, the filaments are bound at both ends and form loops that extend radially outwardly from the skirt. As used herein, the term "loop" refers to a closed or partially open curve formed by a yarn or other filament. In some embodiments, the yarns that form the loops extend from and return to the same fabric portion of the skirt. In such configurations, the loops can be arranged in one or more rows extending circumferentially around the skirt. In other configurations, the yarns extend from one fabric portion to another spaced-apart fabric portion such that the loops are arrayed circumferentially around the valve and are oriented along a longitudinal axis of the valve. In still other embodiments, the filaments are bound at one end, and have free ends that extend outwardly from the skirt.

In such configurations, the filaments can be configured to slow retrograde blood flow past the valve. Features such as the diameter, shape, surface texturing, coatings, etc., of the filaments can induce thrombus formation around the filaments to enhance the sealing properties of the skirt.

Figure 1:
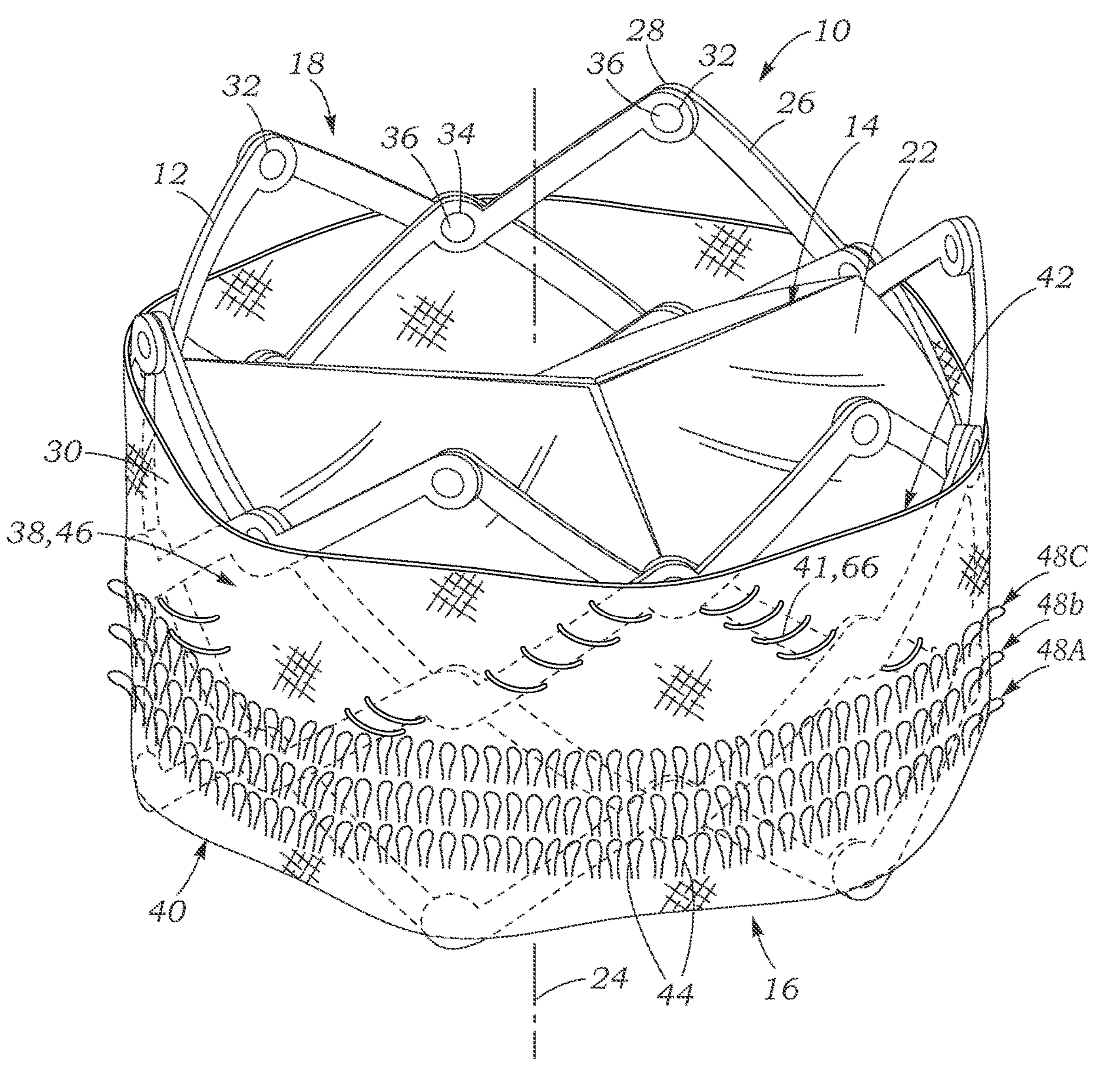
FIG. 1 is a perspective view of a prosthetic heart valve including a representative embodiment of a paravalvular leakage seal including looped filaments.

FIG. 1 illustrates an exemplary embodiment of a radially collapsible and expandable prosthetic valve 10 shown in its deployed, expanded configuration. The prosthetic valve can include an annular stent or frame 12, and a leaflet structure 14 situated within and coupled to the frame 12. The frame 12 can have an inflow end portion 16 and an outflow end portion 18. The leaflet structure can comprise a plurality of leaflets 22, such as three leaflets arranged to collapse in a tricuspid arrangement similar to the aortic valve. Alternatively, the prosthetic valve can include two leaflets 22 configured to collapse in a bicuspid arrangement similar to the mitral valve, or more than three leaflets, depending upon the particular application. The prosthetic valve 10 can define a longitudinal axis 24 extending through the inflow end portion 16 and the outflow end portion 18.

The frame 12 can be made of any of various biocompatible materials, such as stainless steel or a nickel titanium alloy ("NiTi"), for example Nitinol. With reference to FIG. 1, the frame 12 can include a plurality of interconnected lattice struts 26 arranged in a lattice-type pattern and forming a plurality of apices 28 at the outflow end 18 of the prosthetic valve. The struts 26 can also form similar apices at the inflow end 16 of the prosthetic valve (which are covered by a skirt 30 described in greater detail below). The lattice struts 26 are shown positioned diagonally, or offset at an angle relative to, and radially offset from, the longitudinal axis 24 of the prosthetic valve. In other implementations, the lattice struts 26 can be offset by a different amount than depicted in FIG. 1, or some or all of the lattice struts 26 can be positioned parallel to the longitudinal axis of the prosthetic valve.

The lattice struts 26 can be pivotably coupled to one another. In the illustrated embodiment, for example, the end portions of the struts 26 forming the apices 28 at the outflow end 18 and at the inflow end 16 of the frame can have a respective opening 32. The struts 26 also can be formed with apertures 34 located between the opposite ends of the struts. Respective hinges can be formed at the apices 28 and at the locations where struts 26 overlap each other between the ends of the frame via fasteners 36, which can comprise rivets or pins that extend through the apertures 32, 34. The hinges can allow the struts 26 to pivot relative to one another as the frame 12 is expanded or contracted, such as during assembly, preparation, or implantation of the prosthetic valve 10. For example, the frame 12 (and, thus, the prosthetic valve 10) can be manipulated into a radially compressed or contracted configuration, coupled to a delivery apparatus, and inserted into a patient for implantation. Once inside the body, the prosthetic valve 10 can be manipulated into an expanded state and then released from the delivery apparatus, as described in greater detail below with reference to FIG. 21. Additional details regarding the frame 12, the delivery apparatus, and devices and techniques for radially expanding and collapsing the frame can be found in U.S. Publication No. 2018/0153689, which is incorporated herein by reference.

As illustrated in FIG. 1, the prosthetic valve 10 can include a sealing element configured as a skirt 30. The skirt 30 can be configured to establish a seal with the native tissue at the treatment site to reduce or prevent paravalvular leakage. The skirt 30 can include a main body portion 38 disposed about an outer circumference of the frame 12. The skirt 30 can be secured to the frame by, for example, a plurality of sutures 41 extending in a zig-zag pattern along selected strut members 26 between a first edge portion (e.g., an inflow edge portion) 40 and a second edge portion (e.g., an outflow edge portion) 42 of the skirt 30. For example, in certain embodiments the skirt 30 can be sutured to the frame 12 along a suture line 66 corresponding to a scalloped edge defined by the leaflets 22, which can allow the valve to radially expand and contract without interference from, or pinching of, the skirt. Further details regarding transcatheter prosthetic heart valves, including the manner in which the leaflets 22 can be coupled to the frame 12 can be found, for example, in U.S. Pat. Nos. 6,730,118, 7,393,360, 7,510,575, 7,993,394, and 8,652,202, which are incorporated herein by reference in their entireties.

In the illustrated embodiment, the skirt 30 can comprise a plurality of outwardly extending filaments configured as loops 44 (also referred to as looped filaments). The loops 44 can extend from an outer surface 46 of the main portion 38. In certain embodiments, the loops 44 can be arranged in rows or tiers 48 that extend circumferentially around the frame 12, and are spaced apart from one another along the longitudinal axis 24. For example, in the illustrated embodiment, the loops 44 are arranged in three rows 48, with a first row 48A being adjacent the inflow edge portion 40 of the skirt, and the rows 48B, 48C being located above the first row 48A along the longitudinal axis 24 of the valve. In other embodiments, the skirt 30 can include more or fewer rows of loops, depending upon the particular characteristics desired. For example, the skirt 30 can include a single row of loops 44 (e.g., adjacent the inflow end of the frame), or a plurality of rows of loops along substantially the entire height dimension of the skirt 30.

Figure 2:
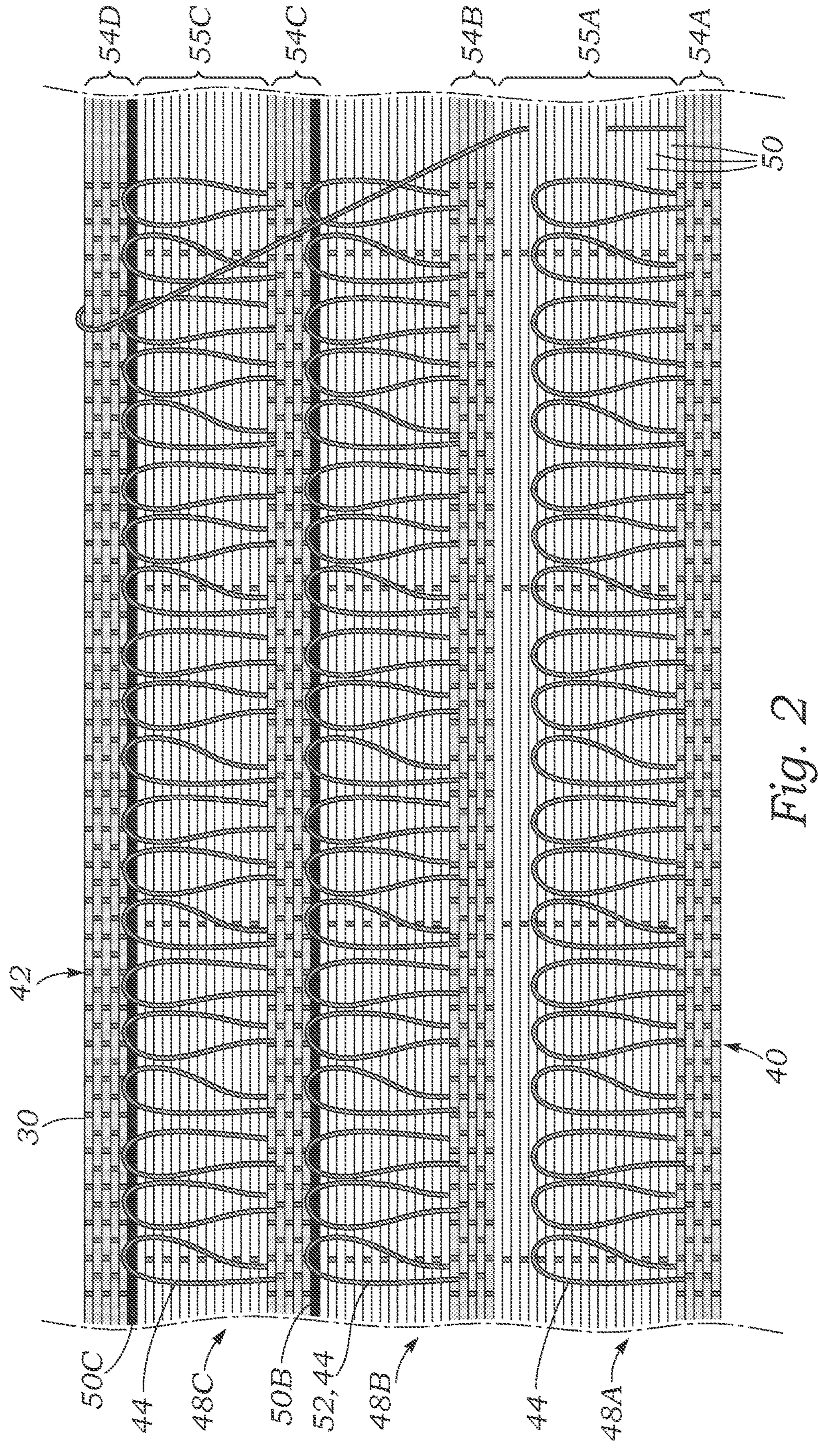
FIG. 2 is a perspective view of the paravalvular leakage seal of FIG. 1.

In particular embodiments, the skirt 30 can comprise a cloth material, such as a woven or knitted fabric. FIG. 2 illustrates a portion of a representative embodiment of the skirt 30 made from such a fabric in greater detail. The fabric can comprise a plurality of first yarns 50 oriented horizontally in FIG. 2 and one or more second yarns 52 oriented vertically in FIG. 2 and selectively interwoven with the first yarns 50 on a loom. In certain configurations, the first yarns 50 can be warp yarns, meaning that during the weaving process the yarns 50 are held by the loom, while the second yarns 52 are weft yarns, which are interwoven with the warp yarns by a moving shuttle or weft-carrying mechanism during the weaving process. However, in other embodiments the first yarns 50 may be weft yarns and the second yarns 52 may be warp yarns. In the illustrated configuration, the fabric comprises a single weft yarn 52 that is selectively interwoven with the warp yarns 50 to form the looped filaments 44, although in other embodiments more than one weft yarn may be used.

Figures 3, 4:
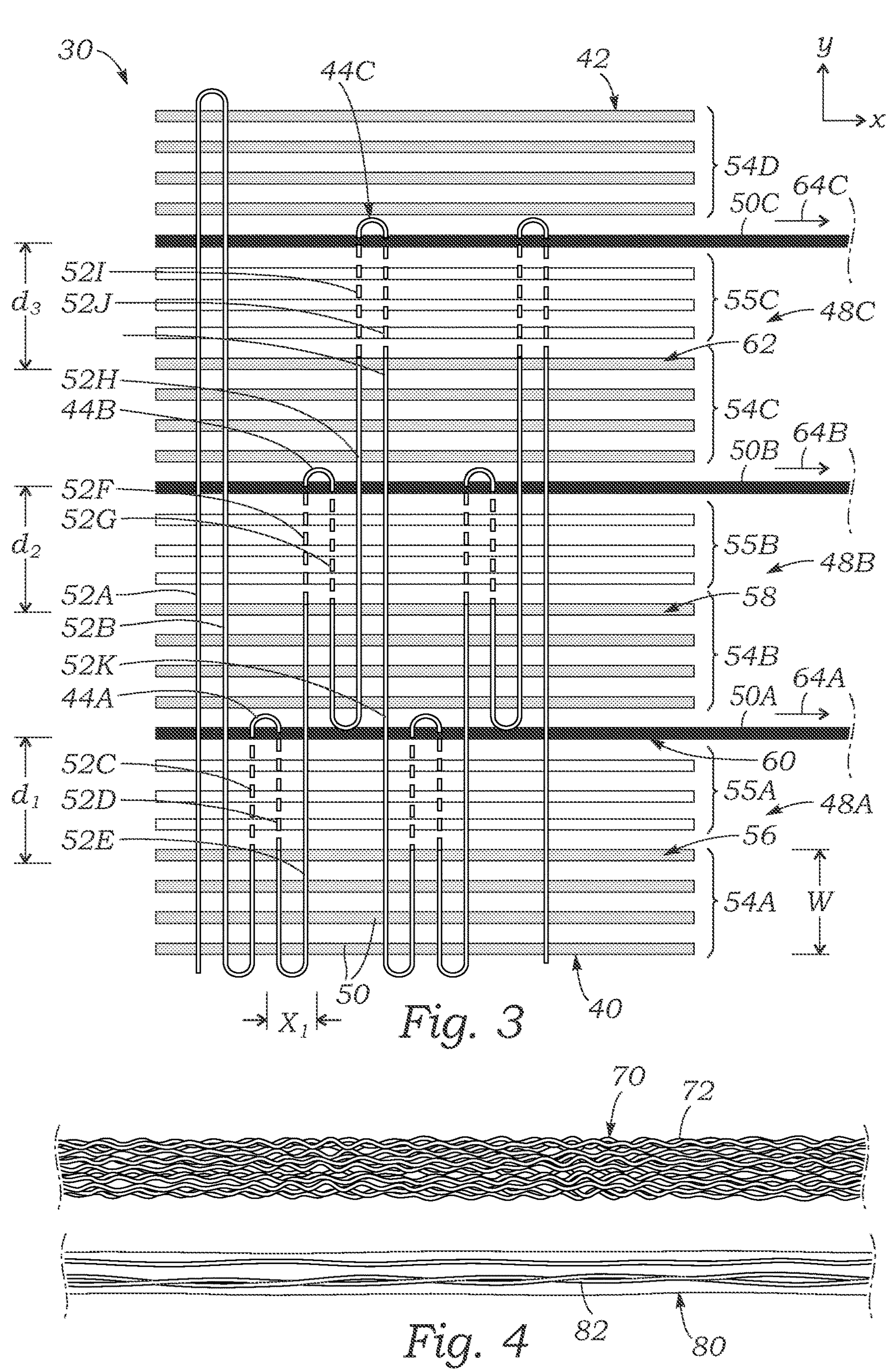
FIG. 3 is a schematic illustration of a representative method of weaving the paravalvular leakage seal of FIG. 1.
FIG. 4 is a side elevation view illustrating a textured yarn and a fully drawn yarn.

FIG. 3 illustrates an exemplary weaving pattern that can be used to produce the skirt 30. With reference to FIG. 3, a first portion 52A of the weft yarn can extend over and under the warp yarns in the fabric from the first edge portion 40 to the second edge portion 42. At the second edge portion 42, the weft yarn 52 doubles back, and a second portion 52B of the weft yarn extends over and under each of the warp yarns in the fabric in a direction back toward the first edge portion 40 in the manner of a plain weave. This can define a side edge of the fabric, and prevent the fabric from unraveling when removed from the loom. At the first edge portion 40, the weft yarn 52 can double back again such that a third portion 52C extends over and under the warp yarns 50 of a first woven portion configured as a fully woven strip 54A of the fabric. In the illustrated configuration, the fabric can include four such woven strips 54A-54D spaced apart from one another between the first and second edge portions 40, 42, and extending parallel to the warp yarns 50. The woven strips 54A-54D can be spaced apart by respective partially or semi-woven portions 55A-55C (also referred to as intermediate sealing portions). In the fully woven strips 54A-54D, every pass of the weft yarn 52 can be incorporated into the weave. In contrast, in the semi-woven portions 55A-55C, only a portion of the passes of the weft yarn are incorporated into the weave. In certain examples, in the woven strips 54A-54D, the warp and weft yarns 50, 52 are woven together in a plain weave (or another suitable weave). In other embodiments, the skirt 30 need not include the woven portion 54D above the last row of loops 44, depending upon the particular application.

Still referring to FIG. 3, at an upper edge 56 of the woven strip 54A, the portion 52C of the weft yarn can exit the weave (e.g., the yarn portion 52C is "dropped" from the weave) and can extend or "float" above the warp yarns 50 of the semi-woven portion 55A for a distance $d_1$. In FIG. 3, portions of the weft yarn 52 that are incorporated into the weave are illustrated in solid lines, and portions of the weft yarn 52 that are not incorporated into the weave (such as portion 52C) are illustrated in dashed lines. The portion 52C can then loop around a removable warp yarn 50A (also referred to as a selvedge yarn), and a fourth portion 52D can extend back toward the first edge portion 40 above the warp yarns and out of the weave. When the weft yarn portion 52D reaches the woven strip 54A, the portion 52D can be reincorporated into the weave such that the warp yarns of the woven strip 54A extend over and under the weft yarn portion 52D.

At the first edge portion 40, the warp yarn 52 can double back again, and a fifth portion 52E can extend in a direction toward the second edge portion 42. The fifth portion 52E can be incorporated into the weave through the semi-woven portion 55A and the woven strip 54B until it reaches an upper edge 58 of the woven strip 54B, at which point a sixth portion 52F can exit, or be "dropped" from, the weave. The sixth portion 52F can extend or float above the warp yarns 50 of the semi-woven portion 55B for a distance $d_2$ in a direction toward the second edge portion 42. The sixth portion 52F can then loop around a removable warp yarn 50B, and a seventh portion 52G of the weft yarn can extend in a direction back toward the first edge portion 40 outside of the weave.

When the seventh portion 52G reaches the upper edge 58 of the woven strip 54B, the seventh portion 52G can be reincorporated into the weave such that the warp yarns of the woven strip 54B extend over and under the seventh portion 52G. When the seventh portion 52G reaches a lower edge portion 60 of the woven strip 54B, the weft yarn can double back, and an eighth portion 52H can extend in a direction toward the second edge portion 42. The eighth portion 52H can be incorporated into the weave through the semi-woven portion 55B and the woven strip 54C until the eighth portion reaches an upper edge portion 62 of the woven strip 54C. At this point, a ninth portion 52I can exit the weave and extend a distance $d_3$ over the warp yarns 50 of the semi-woven portion 55C toward the second edge portion 42. At the woven strip 54D, the ninth portion 52I can loop around a removable warp yarn 50C, and a tenth weft yarn portion 52J can extend back toward the first edge portion 40 outside of the weave.

When the tenth portion 52J reaches the upper edge 62 of the woven strip 54C, the weft yarn can be reincorporated into the weave such that an eleventh weft yarn portion 52K extends back to the first edge portion 40 in the weave. When the portion 52*k* reaches the first edge portion 40, the weft yarn can double back, and the foregoing pattern can be repeated along a length of the fabric (e.g., to the right in FIG. 3). FIG. 3 illustrates two complete instances of the foregoing weave pattern.

When the weave pattern has been repeated a selected number of times (e.g., to produce a fabric having length corresponding to the circumference of the prosthetic valve), the removable warp yarns 50A-50C can be removed from the weave. For example, in the embodiment illustrated in FIG. 3, the warp yarns 50A-50C can be pulled out of the fabric in the direction of respective arrows 64A-64C. This can cause the portions of the weft yarn 50 that are outside the weave to be released from the fabric, thereby forming the loops 44. For example, when the removable warp yarn 50A is removed from the weave, the portions 52C and 52D of the weft yarn are released from the fabric, and can form a looped filament 44A in extending from the woven strip 54A (e.g., in the manner of terrycloth). Likewise, removing the warp yarn 50B can release the weft yarn portions 52F and 52G such that they form a looped filament 44B extending from the woven strip 54B, and removing the warp yarn 50C can release the weft yarn portions 52I and 52J such that they form a looped filament 44C extending from the woven strip 54C.

Thus, removing the warp yarns 50A-50C results in a plurality of looped filaments 44 arranged in the three rows 48A-48C extending lengthwise along the skirt 30, as described above. FIG. 2 illustrates the skirt 30 with the removable warp yarn 50A removed for purposes of illustration. Returning to FIG. 3, and referring to the Cartesian x- and y-axes for reference, the rows 48A-48C of loops 44 can be offset from each other in a direction along the y-axis (e.g., parallel to the longitudinal axis of the valve) by a distance equal to the length of the loops plus the width of the woven strip 54 from which the loops extend. For example, the first row 48A of loops 44 adjacent the first edge portion 40 is offset from the second row 48B of loops by a distance equal to a width W of the woven strip 54A plus the distance $d_1$, the length of the loops 44.

Meanwhile, although the loops 44 are shown axially aligned in FIG. 1 for purposes of illustration, the loops 44 can also be spaced apart from one another in a direction along the x-axis (e.g., circumferentially around the prosthetic valve when the skirt 30 is secured to the valve). For example, in the embodiment illustrated in FIG. 3, a center or apex of the loop 44B is spaced apart from a center or apex of the loop 44A by a distance $x_1$ corresponding to, for example, the distance along the x-axis occupied by the weft yarn portions 52D and 52E in the weave. Thus, in the illustrated configuration, each loop 44 is offset from the next sequential loop 44 in the neighboring rows in a direction along the x-axis by the distance $x_1$. Thus, the loop 44A is offset from the loop 44B by the distance $x_1$ in the negative x direction, and the loop 44C is offset from the loop 44B by the distance $x_1$ in the positive x direction. Loops 44 in the same row are offset from each other along the x-axis by a distance equal to $3x_1$.

In certain embodiments, when the fabric has been removed from the loom and the removable warp yarns 50A-50C have been removed from the weave, the loops 44 can be shape-set such that they extend out of the plane of the fabric (e.g., transverse to the longitudinal axis of the valve and, thus, to the direction of flow through the valve). For example, referring again to FIG. 1, the loops 44 can be shape-set such that they extend radially outwardly from the surface 46 of the skirt 30 at an angle when the skirt is secured to the frame.

In certain configurations, one or both of the warp and weft yarns 50, 52 can also comprise textured yarns. A representative example is illustrated in FIG. 4, which shows an exemplary textured yarn 70 and a fully drawn yarn 80. The textured yarn 70 includes a plurality of constituent fibers 72 that have been crimped, coiled, crinkled, looped, etc., such that the fibers are not as tightly bundled as the fibers 82 of the fully drawn yarn 80. This can increase the surface area of the textured yarn 70, which can improve the blood clotting properties of the yarn, as further described below. Additionally, the fibers 72 from which the yarns 50, 52 are formed can be sized to promote a biological response or interaction at the cellular level between the yarns 50, 52 and the blood flowing past the skirt.

For example, blood cells typically range in size from 2 μm to 15 μm. For example, the diameter of red blood cells typically ranges from 6 μm to 8 μm, and the diameter of platelets typically ranges from 2 μm to 3 μm. Thus, utilizing fibers 72 having a diameter sized to approximately match the diameter of blood cells (e.g., 1 μm to 20 μm) can promote interaction between the fibers and blood cells at the cellular level. For example, the fibers 72 can be configured to promote thrombus formation along the skirt 30, and along the looped filaments 44 in particular, thereby improving the sealing characteristics of the skirt.

In certain configurations, the warp and weft yarns can comprise a variety of biocompatible materials, such as natural fibers (e.g., silk, cotton, etc.), synthetic polymeric materials (e.g., polyethylene terephthalate (PET), Nylon, polytetrafluoroethylene (PTFE), etc.), or metals (e.g., Nitinol, gold, etc.). In other embodiments, the skirt 30 need not comprise a woven fabric, but can comprise a thin polymeric film or laminate with which the looped filaments are integrally formed, or to which the looped filaments are attached.

The skirt 30 can provide a number of significant advantages over known skirt embodiments. For example, the loops 44 can obstruct the flow of blood past the valve, reducing the velocity and volume of blood that leaks past the valve after implantation. The flow obstruction provided by the loops 44 can increase the dwell time of blood near the skirt. This, together with the fiber diameters described above, can induce thrombus formation and promote sealing between the skirt and the surrounding tissue.

Additionally, the loops 44 can be flexible, allowing the loops to conform to the shape of the surrounding anatomy. Because the loops 44 extend radially outwardly from the surface of the skirt 30, the free end portions of the loops can also extend into folds and crevices in the surrounding anatomy to promote a more complete seal. Moreover, when the prosthetic valve is implanted in the native aortic valve, blood around the exterior of the valve can apply force to the loops 44 during ventricular diastole in a direction that is opposite to the direction of blood flow through the valve. This can enhance the bending of the loops 44 away from the skirt 30, further enhancing the sealing properties. Additionally, by extending outwardly from the exterior of the valve, the loops 44 can also block thrombi from moving past the valve, reducing the likelihood of stroke.

Figures 5, 6:
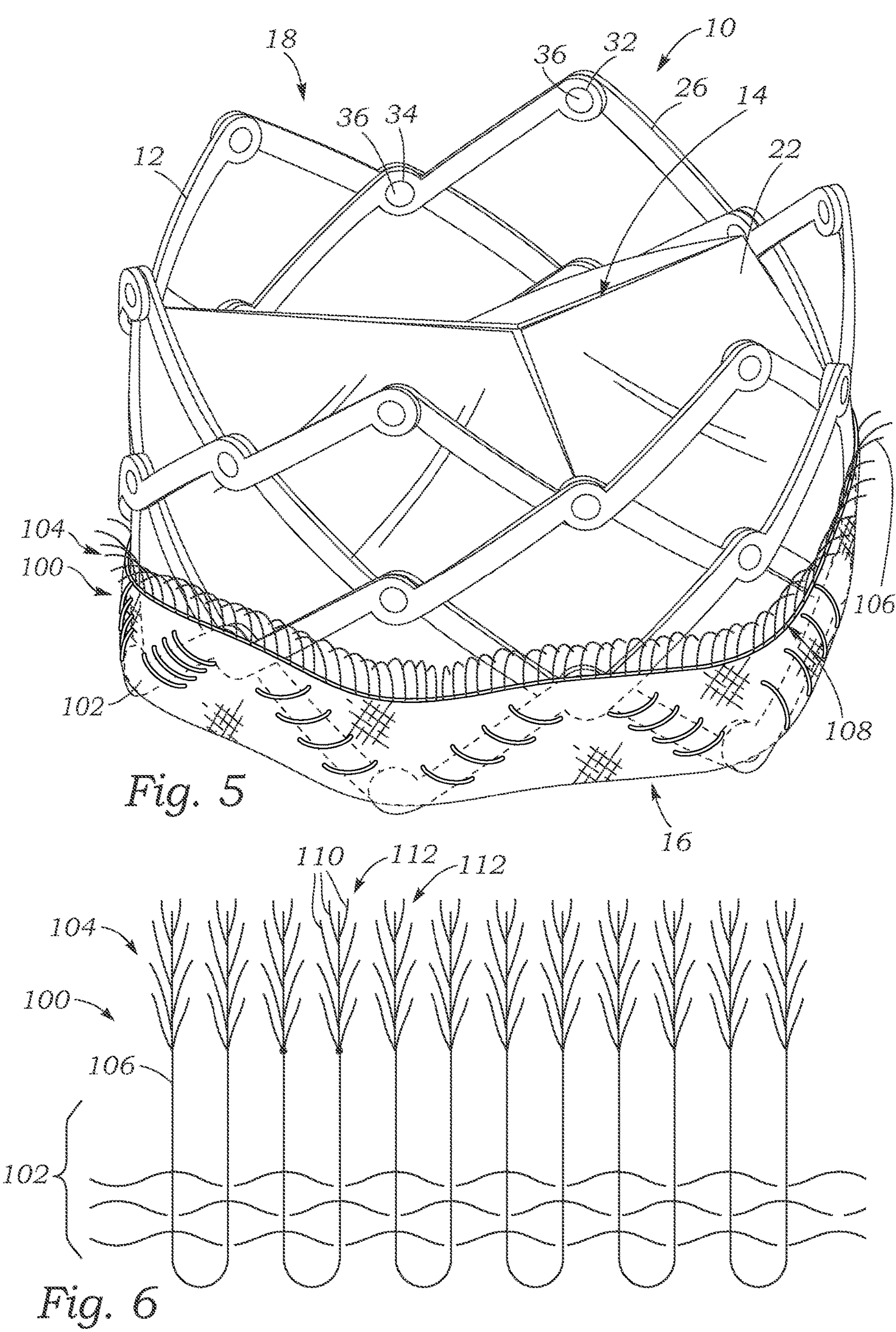
FIG. 5 is a perspective view illustrating a prosthetic heart valve including another embodiment of a paravalvular leakage seal including a woven portion and a plurality of filaments extending from the woven portion.
FIG. 6 is a schematic illustration of the paravalvular leakage seal of FIG. 5.

FIG. 5 illustrates a prosthetic valve 10 including another embodiment of a sealing member or skirt 100. In the illustrated embodiment, the skirt 100 can comprise a woven portion configured as a fabric strip 102, and a fringe portion 104 comprising a plurality of filaments configured as yarns 106 extending from an edge portion 108 of the fabric strip 102. In certain examples, the yarns 106 can be warp yarns extending from the weave of the fabric strip 102 which are not interwoven with any weft yarns, or vice versa. In some embodiments, the yarns 106 can be frayed yarns. For example, the yarns 106 can comprise a plurality of fibers or threads spun together.

FIG. 6 schematically illustrates a portion of such a skirt 100 in greater detail. In the configuration illustrated in FIG. 6, the yarns 106 can be frayed such that the constituent fibers 110 of the yarns are separated from one another and form fan-like structures 112. For example, in some embodiments, the fibers 110 of the yarns 106 can have diameters of 1 μm to 20 μm, a size at which electro-static forces between the fibers can dominate gravitational forces, causing the fibers to splay apart. This can increase the surface area of the yarns 106, which can promote a biological response at the cellular level between blood and the fibers 110 of the skirt, as described above with respect to the embodiment of FIG. 1. Thus, the fibers 110 can be configured to promote thrombus formation along the fringe portion 104, thereby improving the sealing characteristics of the skirt 100.

In certain embodiments, the yarns 106 can comprise any of a variety of hydrophobic surface treatments or coatings in order to promote separation of the fibers 110 and increase the surface area of the fringed portion 104. In other embodiments, the yarns 106 can comprise hydrophilic surface treatments, such as polyethylene glycol (PEG), or other coatings that covalently bond to the fibers. The yarns 106 can also comprise coatings or treatments to promote a biological response (e.g., thrombus formation) from blood in contact with the yarns, and/or lubricious coatings such as Serene™ lubricious coatings available from Surmodics, Inc. In other embodiments, an electrostatic charge can be applied to the yarns 106 such that the fibers 110 repel each other to increase the separation of the fibers. In still other embodiments, the fibers 110 can be textured fibers, as described above with respect to the embodiment of FIG. 1, or coated or felted with short-length, small diameter fibers. In other examples, the yarns 106 can also form loops.

Figures 7, 8:
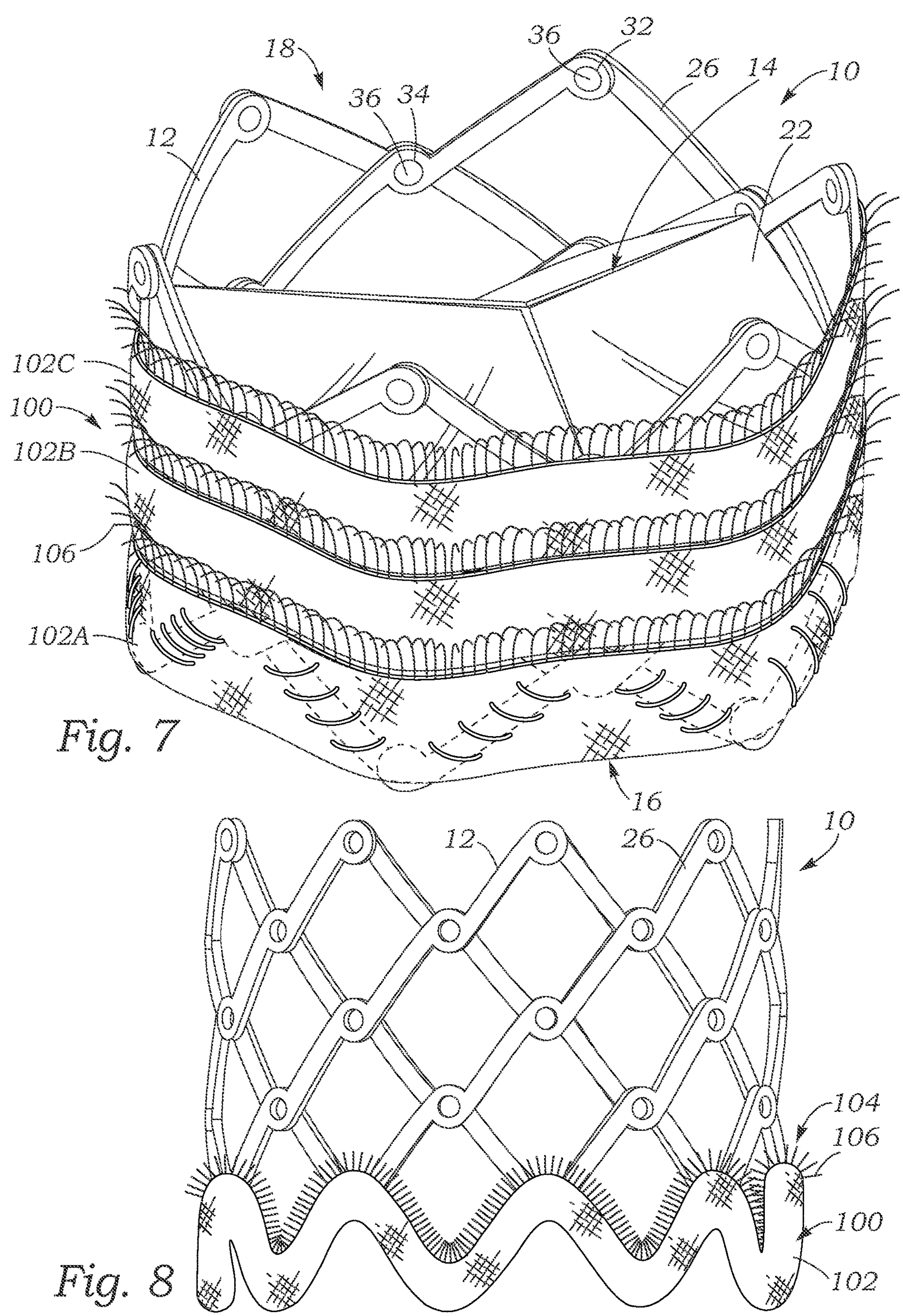
FIG. 7 is a perspective view of the prosthetic heart valve of FIG. 5 including another embodiment of the paravalvular leakage seal including a plurality of woven portions arranged in a tiered arrangement on the outside of the valve.
FIG. 8 is a side elevation view of the prosthetic heart valve of FIG. 5 including another embodiment of the paravalvular leakage seal in which the woven portion extends in a zig-zag pattern around the valve parallel to the strut members of the frame.

With reference to FIG. 7, in another configuration, the skirt 100 can comprise multiple fabric strips 102 arranged one on top of the other in a tiered arrangement. For example, in the illustrated embodiment, the skirt 100 can comprise three fabric strips 102A-102C arranged such that the frayed edge portion 108 of each strip is oriented toward the outflow end 18 of the frame. Although the illustrated embodiment includes three fabric strips 102A-102C, the skirt 100 can comprise any suitable number of fabric strips 102 depending upon, for example, the width of the fabric strips, the length of the prosthetic valve, etc. In other embodiments, both longitudinal edges of the fabric strips 102 can comprise yarns 106.

In another configuration illustrated in FIG. 8, the skirt 100 can be secured to the struts 26 such that it extends along the struts and forms a zig-zag shape. Multiple skirts 100 can be secured to the strut members 26 of the frame in this fashion, depending upon the particular application.

Figure 9:
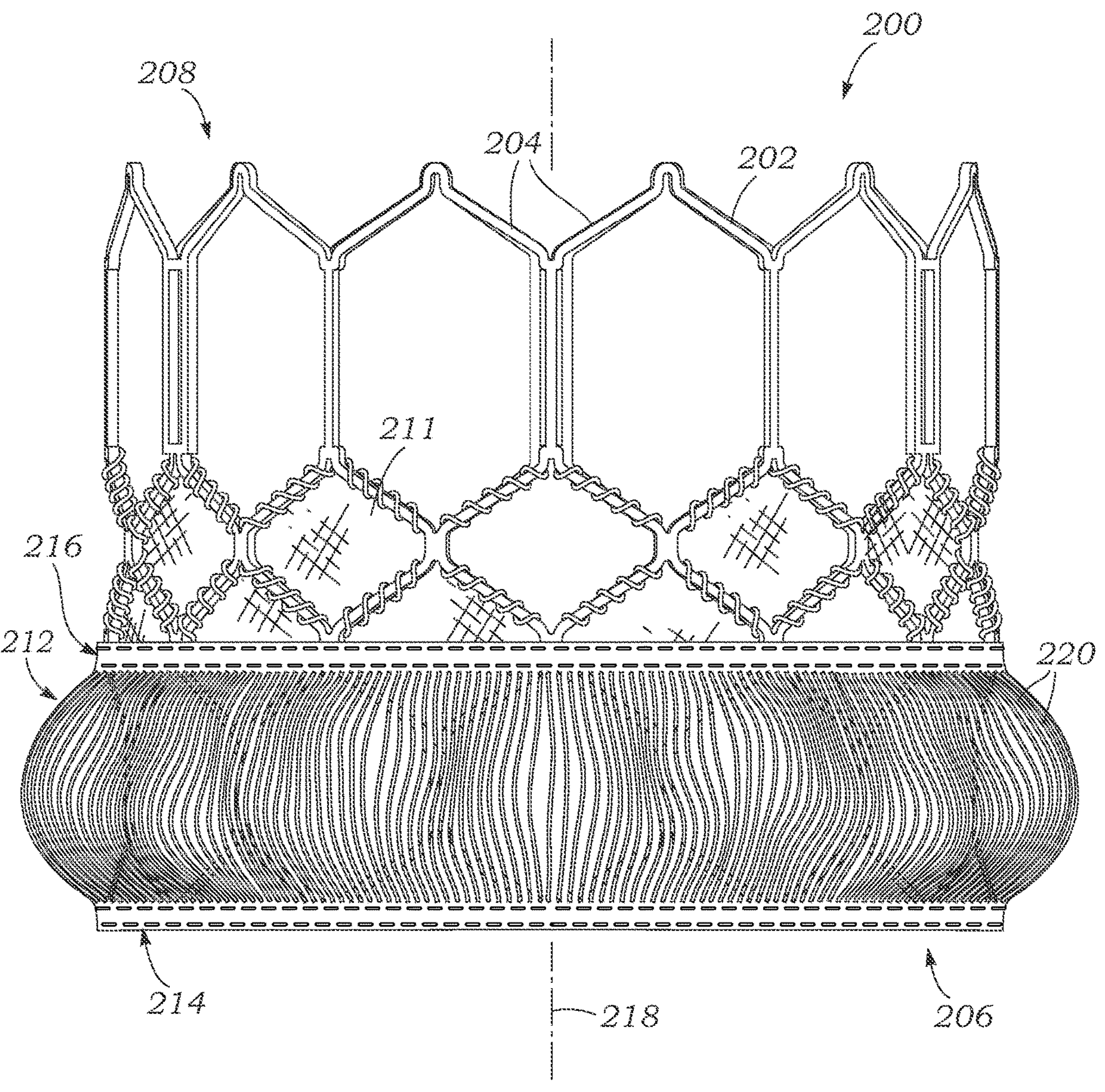
FIG. 9 is a perspective view of another embodiment of a prosthetic heart valve including a paravalvular leakage seal having a first woven portion, a second woven portion, and a plurality of yarns that extend between the first and second woven portions to form loops.

FIG. 9 illustrates another embodiment of a prosthetic valve 200 configured as the Edwards Lifesciences Corporation SAPIEN® 3 prosthetic heart valve described in detail in U.S. Pat. No. 9,393,110, which is incorporated herein by reference. The prosthetic valve 200 includes a radially expandable and collapsible frame 202 formed by a plurality of angled strut members 204, and having an inflow end 206 and an outflow end 208. Although not shown, the prosthetic valve 200 can also include a leaflet structure comprising two leaflets, three leaflets, or any other suitable number of leaflets situated within and secured to the frame as described in U.S. Pat. No. 9,393,110.

The prosthetic valve 200 can comprise an inner skirt 211 secured to an interior surface of the frame, and an outer sealing element configured as a skirt 212 disposed around the exterior of the frame 202. In the illustrated configuration, the skirt 212 can comprise a first circumferentially-extending portion 214 situated adjacent the inflow end 206 of the frame and a second circumferentially-extending portion 216. The circumferential portions 214, 216 can be spaced apart from each other along a longitudinal axis 218 of the frame, and coupled together by a plurality of filaments 220. The filaments 220 can extend longitudinally along the outside of the frame between the portions 214, 216, and can curve outwardly from the frame when the frame is in the expanded configuration to form loops. The looped filaments 220 can be configured to promote sealing by obstructing blood flow past the skirt and increasing the dwell time of blood in the vicinity of the filaments, as described above.

In certain configurations, the circumferential portions 214, 216 can be configured as one or more strips of woven fabric. The filaments 220 can be yarns that are incorporated into the fabric of the portions 214 and 216, and extend axially therebetween. The skirt 212 illustrated in FIG. 9 includes a single layer of looped filaments 220 for ease of illustration, although the skirt embodiments described herein can include two or more layers of looped filaments, depending upon the number of fabric strips incorporated into the portions 214, 216. Increasing the number of looped filaments (e.g., by increasing the number of fabric strips) can increase the overall surface area of the sealing element available for thrombogenesis.

Figures 10, 11, 12A, 12B:
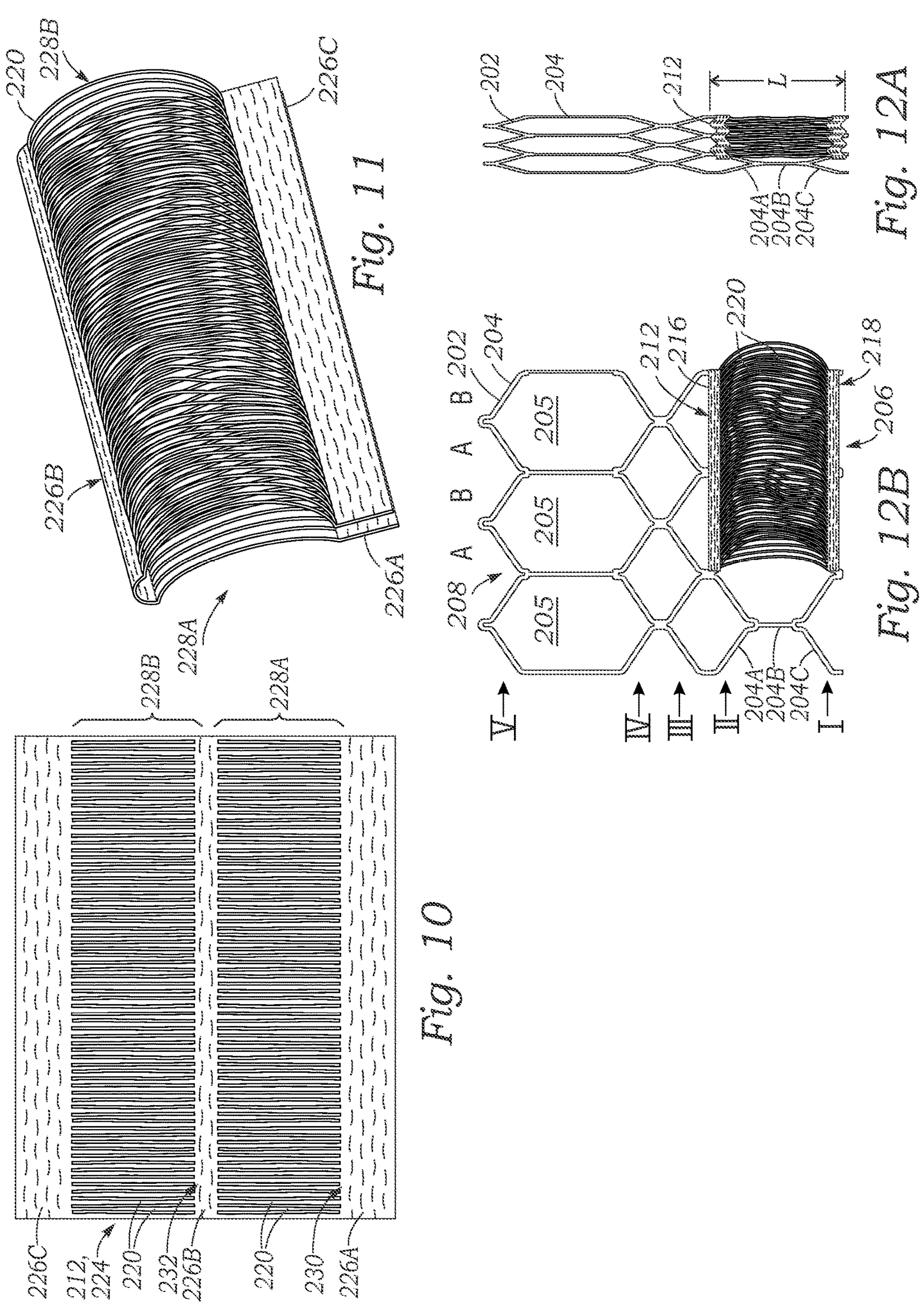
FIG. 10 is a top plan view of a representative embodiment of the paravalvular leakage seal of FIG. 9.
FIG. 11 is a perspective view of the paravalvular leakage seal of FIG. 9 folded over on itself prior to attachment to the prosthetic valve.
FIG. 12A is a side elevation view of a portion of the frame of the prosthetic valve of FIG. 9 in an expanded configuration illustrating the longitudinally-extending yarns of the paravalvular leakage seal curving outwardly from the frame.
FIG. 12B is a side elevation view of the portion of the frame of FIG. 12A in a radially collapsed configuration illustrating the longitudinally-extending yarns of the paravalvular leakage seal pulled straight along a longitudinal axis of the valve.

For example, FIG. 10 illustrates a representative embodiment of a skirt 212 configured to provide two layers of looped filaments 220 when secured to the frame, and laid out flat for purposes of illustration. The skirt 212 can comprise a main body 224 including a first fabric strip 226A, a second fabric strip 226B, and a third fabric strip 226C. The fabric strip 226B can be located between the fabric strips 226A and 226C. The fabric strip 226B can be spaced apart from the fabric strip 226A by a floating yarn portion 228A comprising a plurality of filaments or yarns 220. Likewise, the fabric strip 226C can be spaced apart from the fabric strip 226B by a floating yarn portion 228B comprising a plurality of yarns 220.

In the illustrated configuration, the first fabric strip 226A can comprise warp and weft yarns woven together. At an edge portion 230 of the fabric strip 226A, the yarns 220 can exit the weave and extend or "float" to the second fabric strip 226B to form the floating yarn portion 228A. When the floating yarns 220 reach the second fabric strip 226B, the yarns can be reincorporated into the woven fabric of the strip 226B. At an edge portion 232 of the fabric strip 226B, the yarns 220 can exit the weave again, and extend or float from the strip 226B to the strip 226C to form the floating yarn portion 228B. When the floating yarns 220 reach the fabric strip 226C, they can be reincorporated into the weave of the fabric strip 226C. In certain configurations, the yarns 220 are warp yarns, although the yarns 220 may also be weft yarns, or a combination of warp and weft yarns, depending upon the particular application.

Referring to FIG. 11, the main body 224 of the skirt 212 can be folded about the fabric strip 226B such that the fabric strip 226C is adjacent the fabric strip 226A, and such that the floating yarn portions 228A and 228B are overlaid or coextensive with each other. The folded skirt 212 can then be secured to the frame (e.g., by suturing) such that the fabric strips 226A, 226C form the first portion 214, and the fabric strip 226B forms the second portion 216. In this manner, the longitudinally-extending yarns 220 of the floating yarn portion 228A form a first or radially inward layer of curved yarns or loops, and the longitudinally-extending yarns 220 of the floating yarn portion 228B form a second or radially outward layer of curved yarns or loops (or vice versa). To produce the single layer of looped filaments 220 illustrated in FIG. 9, the skirt 212 need only include, for example, the woven strips 226A and 226B, and the floating yarn portion 228A.

Referring to FIGS. 12A and 12B, which illustrate a portion of the frame 202, the strut members 204 can be arranged end-to-end to form a plurality of rows or rungs of strut members that extend circumferentially around the frame 202. For example, the frame 202 can comprise a first or lower row I of angled strut members forming the inflow end 206 of the frame; a second row II of strut members above the first row; a third row III of strut members above the second row; a fourth row IV of strut members above the third row, and a fifth row V of strut members above the fourth row and forming the outflow end 208 of the frame. The structure and characteristics of the rows I-V of strut members 204 are described in greater detail in U.S. Pat. No. 9,393,110, incorporated by reference above. The strut members 204 of the frame 202 can also be grouped into columns. For example, the frame 202 can include a plurality of first or "type A" columns, and second or "type B" columns arranged alternatingly around the circumference of the frame. In the illustrated configuration, the type A columns comprise the strut members 204 on the left side of the diamond-shaped windows 205 defined by the rows IV and V of strut members, and the strut members extending downwardly therefrom. The type B columns comprise the strut members 204 on the right side of the windows 205, and the strut members extending downwardly therefrom.

With reference to FIGS. 9 and 12A, the first portion 214 of the skirt 212 can be secured (e.g., by suturing) to the first row I of strut members 204 adjacent the outflow end of the frame. The second portion 216 can be secured along the intersection of the second and third rows II and III of struts 204. A length of the yarns 220 can be configured such that the yarns curve radially outwardly from the surface of the frame 202 when the frame is in the expanded configuration and form loops. For example, when coupled to the frame, the skirt 30 can have a length L corresponding approximately to the sum of the lengths of strut members 204A, 204B, and 204C identified in FIG. 12A. In this manner, when the frame 202 is in the radially compressed or crimped configuration (in which the strut members 204A, 204B, and 204C are axially aligned or nearly aligned with one another), the yarns 220 can be pulled straight to reduce the crimp profile of the valve for insertion into a delivery sheath.

In the configuration illustrated in FIGS. 9-12B, the portions 214, 216 of the skirt 212 extend generally parallel to each other and are not angled with respect to the longitudinal axis 218 of the frame. In other configurations, one or both of the portions 214, 216 can be attached to the frame such that they are angled relative to the longitudinal axis 218 of the frame. For example, FIG. 13 illustrates a configuration in which the portion 214 is secured to the first row I of strut members such that the portion 214 extends parallel to the angled strut members 204 around the circumference of the frame 202. In other words, the portion 214 forms a zig-zag pattern along the first row I of strut members 204 that corresponds to the zig-zag pattern of the strut members of the first row I. The portion 216 is secured to the third row III of strut members 204, and also extends parallel to the angled strut members of the third row III.

In embodiments in which the portions 214, 216 of the skirt 212 extend parallel to the strut members 204 of the respective row to which they are secured, the skirt 212 can extend between even-numbered rows of strut members, odd-numbered rows of strut members, or from an odd-numbered row to an even-numbered row, or vice versa. For example, in the configuration illustrated in FIG. 13, the first portion 214 is secured to the first row I, and the second portion 216 is secured to the third row III such that the skirt extends between two odd-numbered rows of strut members. With respect to the frame 202 illustrated in FIGS. 9-15, where the skirt extends from an odd-numbered row to another odd-numbered row (e.g., from row I to row III), or from an even-numbered row to another even-numbered row (e.g., from row II to row IV), the portions 214, 216 can be arranged such that the yarns 220 extend in a direction parallel to the longitudinal axis 218 of the frame. Stated differently, where the skirt 212 extends between odd-numbered rows or between even-numbered rows, a given yarn 220 can extend from a location along the first portion 214 that is secured to a type A column to a location along the second portion 216 that is also secured to a type A column.

In configurations in which the skirt extends from an odd-numbered row to an even-numbered row (or vice versa), the portions 214, 216 can be circumferentially offset from each other such that the yarns 220 extend at an angle to the longitudinal axis 218. For example, with reference to FIG. 14, the first portion 214 is coupled to the first row I of strut members, and the second portion 216 is coupled to the fourth row IV of the strut members. As illustrated in FIG. 14, the first and second portions 214, 216 of the skirt are offset from each other about the circumference of the frame such that a given yarn 220 that extends from a location along the first portion 214 that is secured to a type A column of strut members is coupled to a location along the second portion 216 that is secured to a type B column of strut members. This allows the yarns 220 to extend parallel to the longitudinal axis of the frame when the frame is crimped.

FIG. 15 illustrates another configuration in which the skirt 212 is draped between intersections or apices 234 of the strut members 204 such that the portions 214, 216 hang from the frame 202. For example, in the illustrated configuration the portion 214 is secured to intersections of strut members of row I, and the portion 216 is secured to intersections of the strut members of rows III and IV. One or both of the portions 214, 216 can be secured in this manner, depending upon the particular characteristics desired.

In certain examples, the skirt 212 can comprise twisted yarns, or non-twisted yarns. The skirt 212 can also comprise core-spun yarns, in which wrapper fibers are spun around a core yarn. The wrapper fibers may be wispy or diffuse in order to increase the surface area of the core-spun yarn to promote a biological response, as described above. In certain embodiments, the skirt 212 can also include loops similar to the loops 44 of FIG. 1, in addition to the floating yarn portions 228.

Figures 16A, 16B, 17:
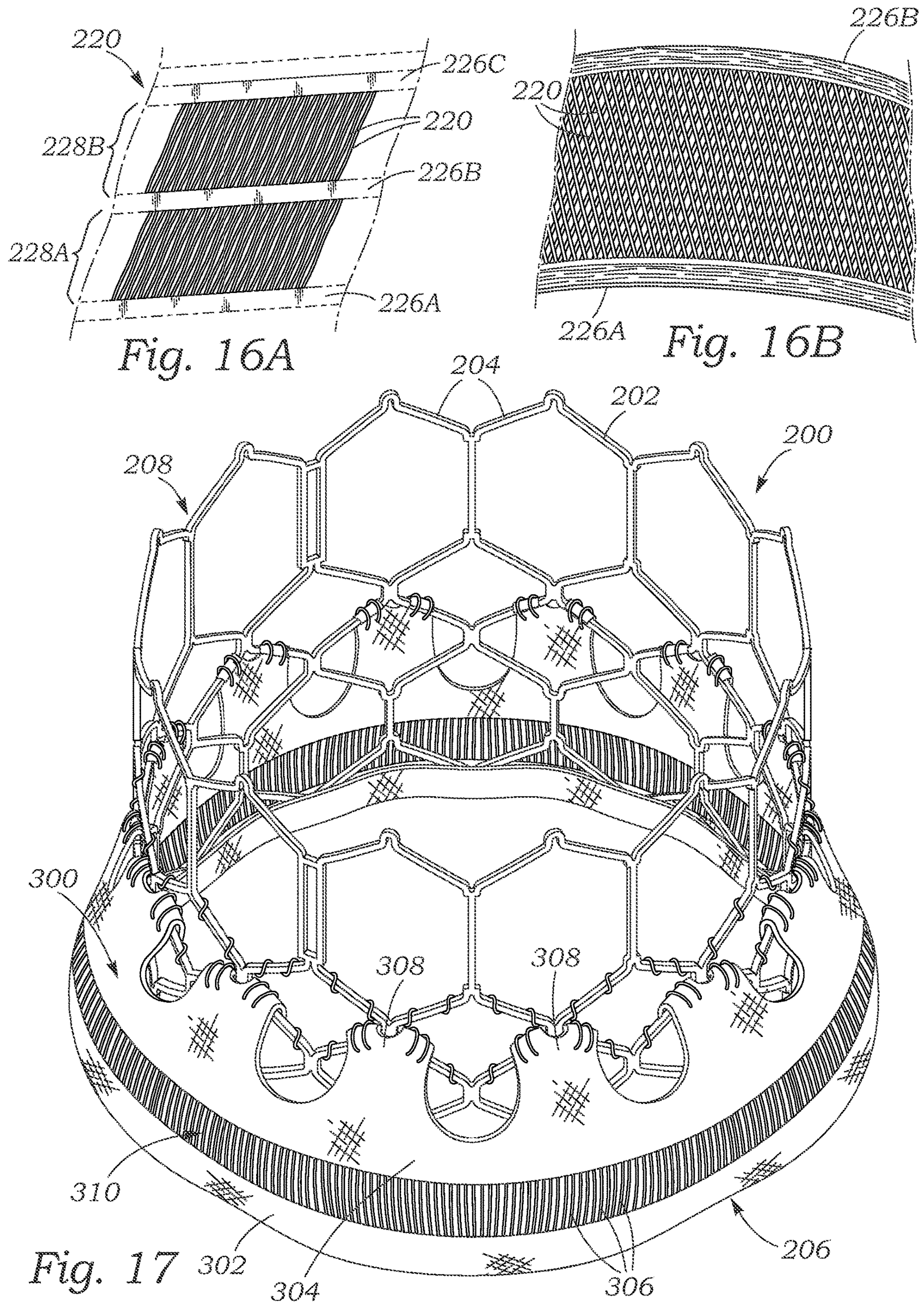
FIGS. 16A and 16B illustrate another embodiment of the paravalvular leakage seal of FIG. 9 in which the longitudinally-extending yarns extend at an angle between the first and second woven portions of the seal.
FIG. 17 is a perspective view of the prosthetic heart valve of FIG. 9 including another embodiment of the paravalvular leakage seal including a single layer of longitudinally-extending yarns.

FIGS. 16A and 16B illustrate another skirt 212 in which the yarns 220 extend between the fabric strips 226A, 226B, and 226C at an angle. For example, referring to FIG. 16A, the yarns 220 of the floating yarn portion 228A extend at an angle to the fabric strips 226A and 226B. The yarns 220 of the floating yarn portion 228B can also extend at an angle to the fabric strips 226B and 226C. In this manner, when the main body 224 is folded, the yarns 220 of the floating yarn portion 228A can be at an angle to or "criss-crossed" with the yarns of the floating yarn portion 228B to form a mesh or web as shown in FIG. 16B. In some embodiments, the yarns can extend at an angle of from 10 degrees to 40 degrees. In certain configurations, having the yarns of the floating yarn portions 228A and 228B cross each other at an angle can reduce the potential for gaps between the yarns resulting from the yarns clustering together. In some embodiments, the yarns of the floating yarn portion 228A and the floating yarn portion 228B can be parallel to each other.

FIG. 17 illustrates the prosthetic valve 200 and frame 202 of FIG. 9 including another embodiment of a skirt 300. The skirt 300 can comprise first and second circumferentially-extending portions 302, 304 spaced apart from each other and coupled together by a plurality of filaments configured as yarns 306 extending longitudinally along the frame, similar to the skirt 212. In the embodiment illustrated in FIG. 17, the portions 302, 304 can be relatively wider than the portions 214, 216 of the skirt 212, such that edge portions of the portions 302, 304 curve outwardly from the frame 202 in the expanded configuration, along with the filaments 306. The second portion 304 can also include a plurality of connection portions 308 extending upwardly (e.g., toward the outflow end 208 of the frame) from the portion 304 and secured to the struts 204 (e.g., by suturing).

Figures 18, 19:
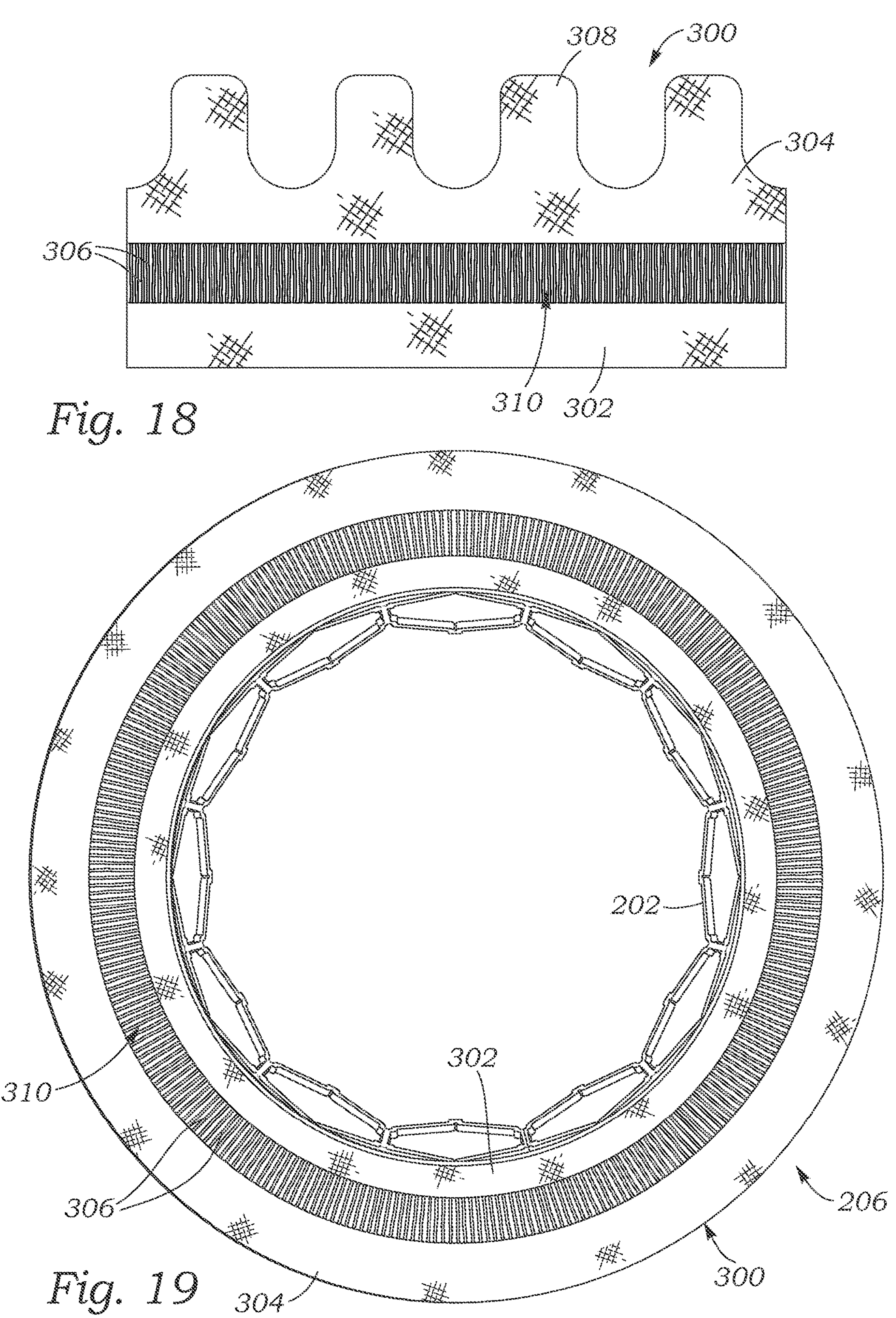
FIG. 18 is a top plan view of a portion of the paravalvular leakage seal of FIG. 17.
FIG. 19 is a bottom plan view of the prosthetic heart valve of FIG. 17.

In the illustrated configuration, the skirt 300 includes a single layer of longitudinally-extending yarns 306. FIG. 18 illustrates a representative configuration of the skirt 300 laid flat before the skirt is attached to the frame. The first and second portions 302, 304 can comprise woven fabric strips, similar to the skirt 212. The fabric portions 302, 304 can be spaced apart by a floating yarn portion 310 through which the yarns 306 extend. In some embodiments, the yarns 306 can be warp yarns, and the floating yarn portion 310 can be formed by omitting the weft yarns from the floating yarn portion, or by removing selected weft yarns from the weave.

When the skirt 300 is secured to the frame, the first portion 302 can be folded around the inflow end portion 206 of the frame 202 such that the first portion is partially disposed within the frame. After implantation, blood can flow through the floating yarn portion 310 and drain from the skirt. In certain configurations, the skirt 300 can have a reduced crimp profile because the skirt is not folded before it is secured to the frame. In other configurations, the portions 302, 304 can be sized such that the floating yarn portion 310 is located on a lower or distal aspect of the skirt when the frame is expanded. For example, FIG. 19 is a perspective view of the distal or inflow end portion of the frame 202 illustrating the yarns 306 located distally of the inflow end portion 206.

Figure 20:
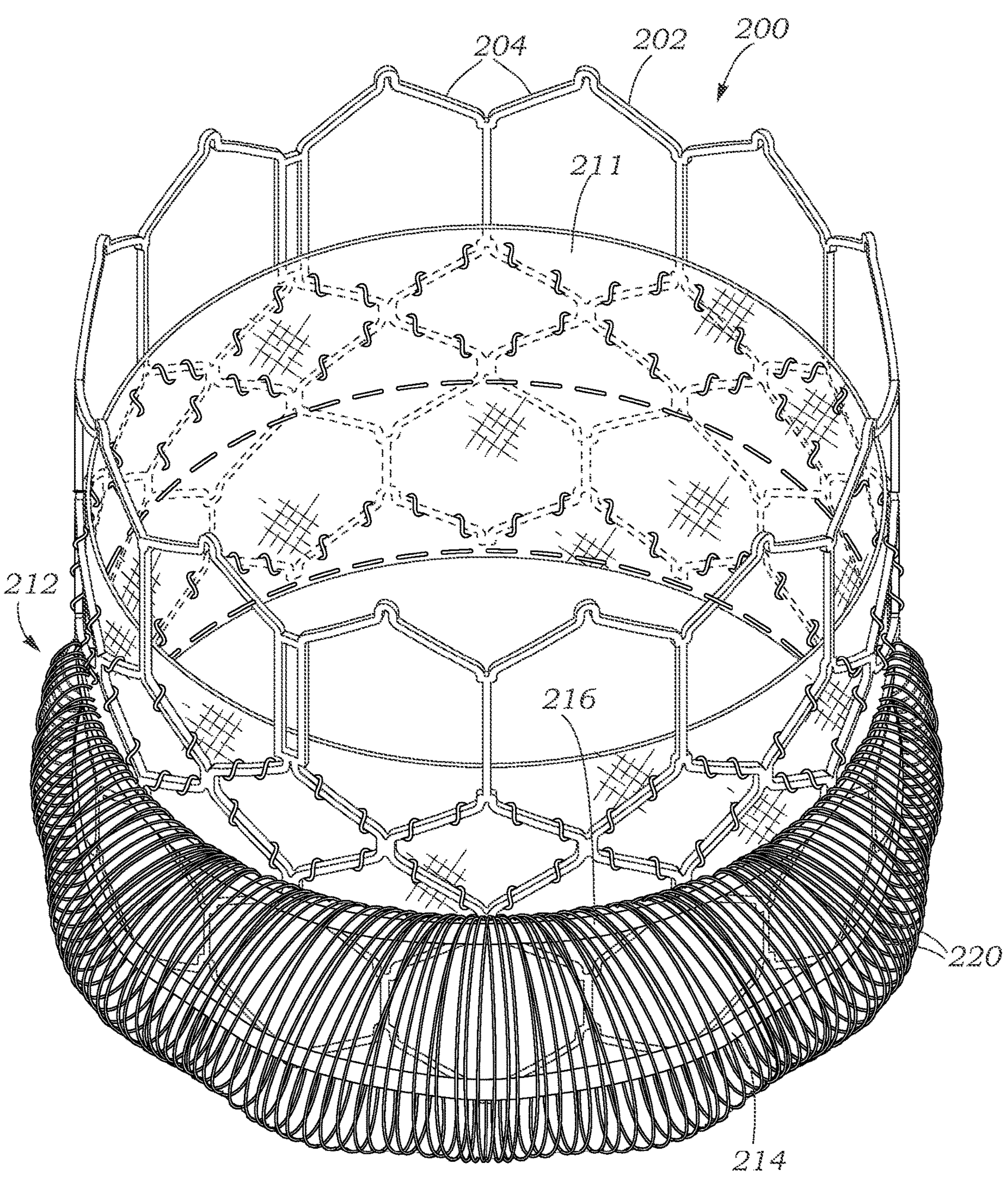
FIG. 20 is a perspective view of the prosthetic heart valve of FIG. 9 including another embodiment of a paravalvular leakage seal.

FIG. 20 illustrates another configuration of the skirt 212 in which the yarns 220 are configured to curve over or around the portions 214, 216 before being reincorporated into the weave. For example, referring to FIGS. 10 and 20, the skirt 212 can be secured to the frame such that the yarns 220 extend from the distal edge portion of the fabric strip 226A, double back and extend proximally and over the fabric strip 226B to the proximal edge portion of the strip 226B such that the yarns form a C-shaped arc. In other embodiments, one or both of the fabric strips 226A, 226B can be omitted, and the yarns 220 can be secured to the frame by being looped through the strut members 204.

Figure 21:
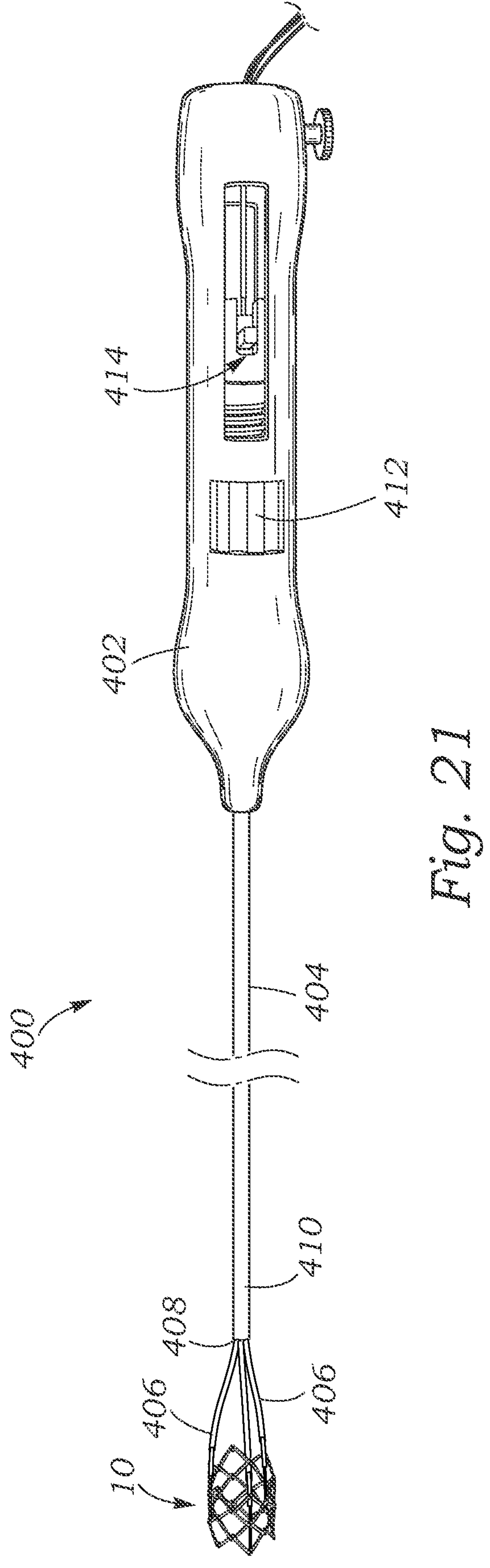
FIG. 21 is a perspective view of a representative embodiment of a delivery apparatus.

The disclosed prosthetic valve embodiments can be radially collapsed and delivered to the heart percutaneously using any of a variety of catheter-based delivery systems. For example, FIG. 21 shows a representative example of a delivery assembly 400 configured for use with the prosthetic valve 10 of FIGS. 1-8 and described in detail in U.S. Publication No. 2018/0153689 incorporated by reference above. The delivery assembly 400 can include a handle 402, an elongate shaft 404 extending distally from the handle 402, and a plurality of actuation members 406 (e.g., in the form of positioning tubes) extending through the shaft and distally outwardly from a distal end 408 of the shaft 404. The actuation members 406 can be coupled to select apices of the valve frame 12.

Initially, the prosthetic valve 10 can be in a radially collapsed configuration within a sheath 410 of the shaft 404. When the distal end of the delivery apparatus has been advanced through the patient's vasculature to the treatment site, the prosthetic valve 10 can be advanced from the sheath 410 using a rotatable actuator 412 on the handle 402. The prosthetic valve 10 can then be positioned at the treatment site, expanded, and deployed using a release assembly generally indicated at 414. Other delivery systems that can be used in combination with the prosthetic valve embodiments described herein can be found in US Patent Application Publication No. 2017/0065415 and US Patent Application Publication No. 2013/0030519, which are incorporated herein by reference.

Figure 22:
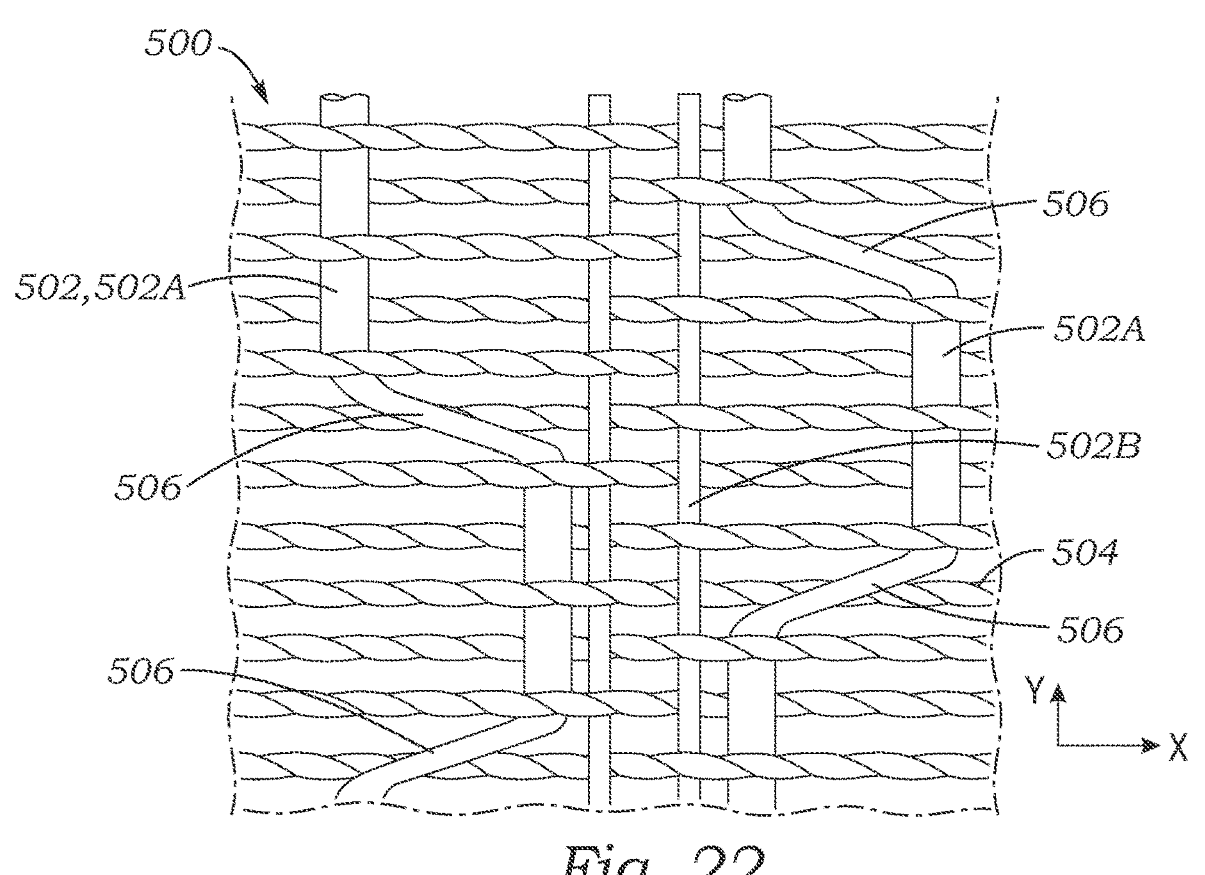
FIGS. 22-25 illustrate various other embodiments of sealing elements with yarns that form loops extending from the sealing elements.

FIGS. 22-25 illustrate additional embodiments of fabric sealing elements that include a plurality of yarns or fibers that extend from the sealing elements to form loops in the manner of a looped pile to increase the surface area available for thrombogenesis and tissue growth. For example, FIG. 22 schematically illustrates a portion of a sealing element 500 including a plurality of first yarns 502 interwoven with a plurality of second yarns 504. In certain embodiments, the first yarns 502 can be warp yarns, and the second yarns 504 can be weft yarns, or vice versa. The warp yarns 502 can be configured to form loops 506 that extend outwardly from the plane of the page, and extend over one or more weft yarns 504. For example, in the embodiment of FIG. 22, the sealing element can comprise warp yarns 502A and warp yarns 502B. The warp yarns 502A can form the loops 506, while one or more warp yarns 502B can be interposed between warp yarns 502A. For example, in the illustrated embodiment, there are two warp yarns 502B between the two warp yarns 502A, although there may be any number of warp yarns 502B depending upon, for example, the desired spacing between the loops 506.

Figure 23:
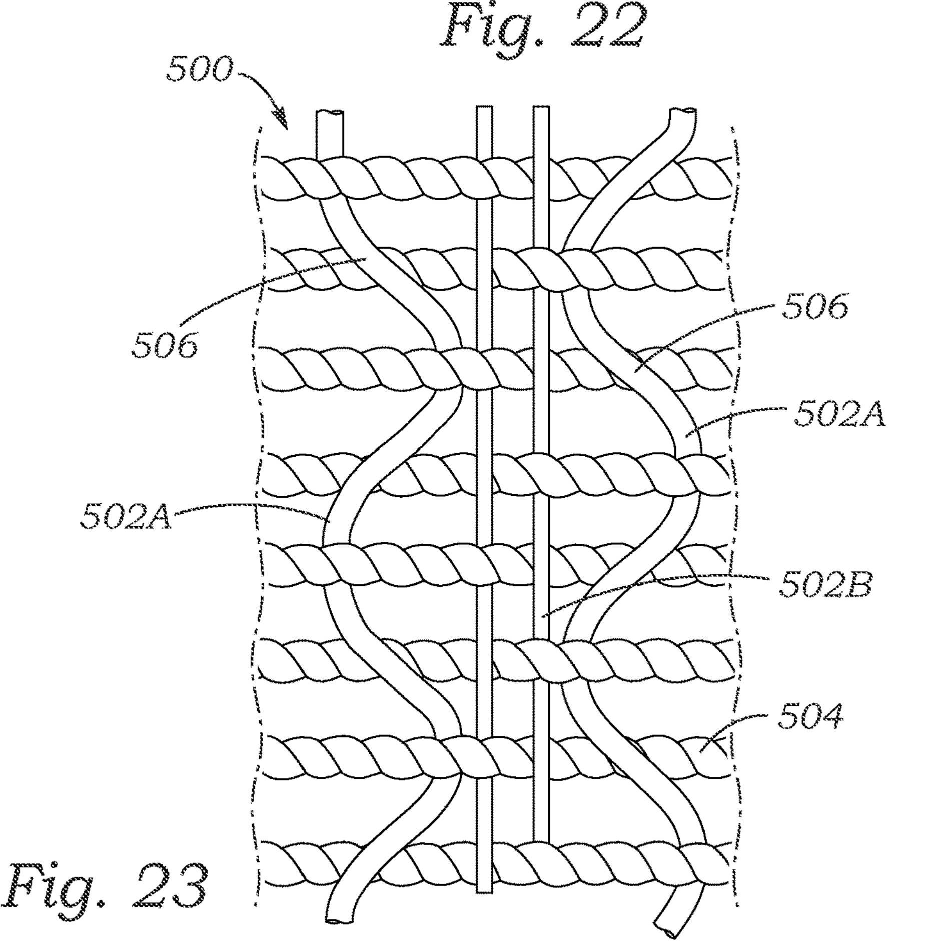
Figures 24, 25:
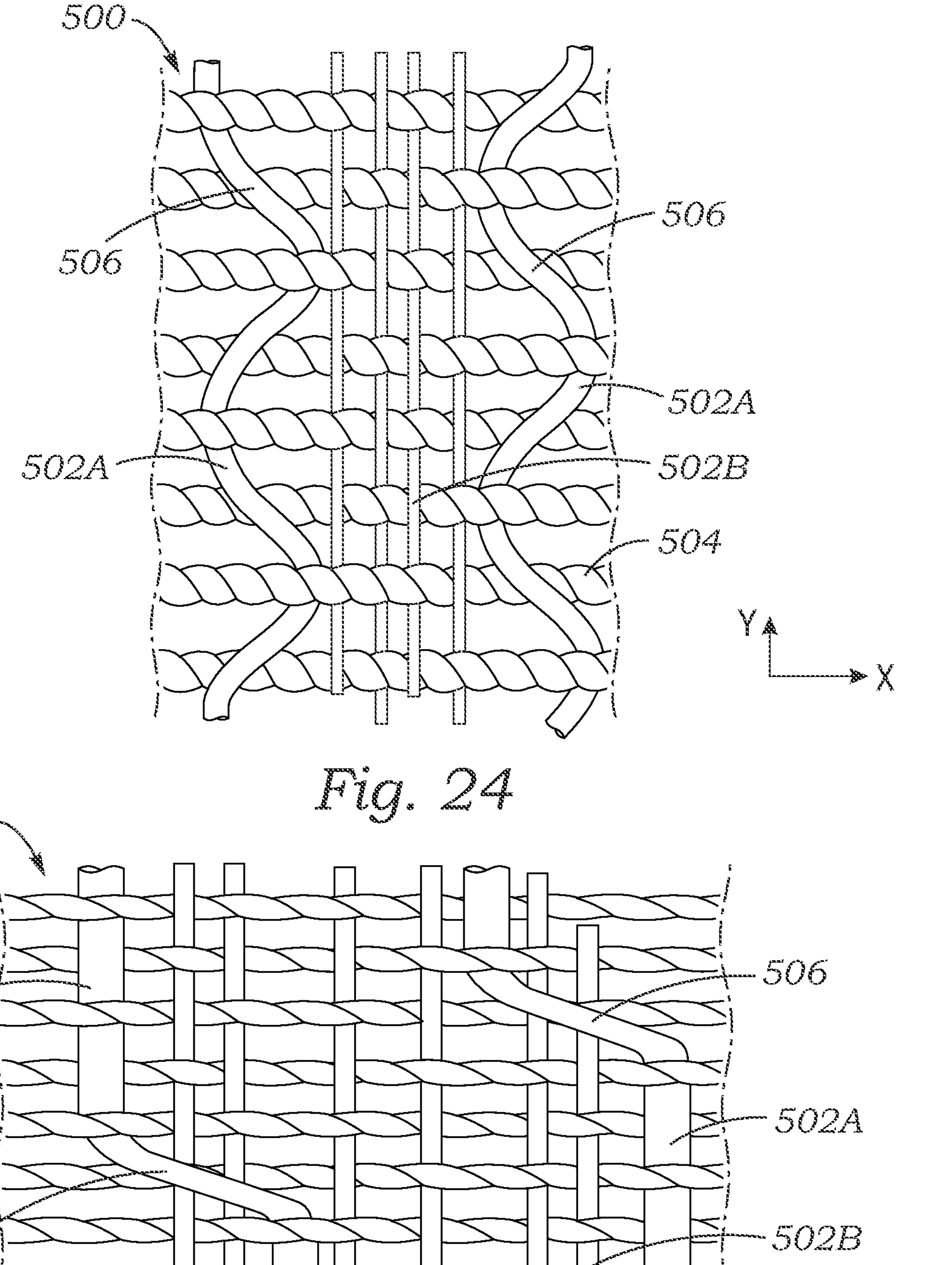

The warp yarns 502A can also change direction where they form the loops 506. For example, in the embodiment of FIG. 22, the loops 506 can extend across one or more weft yarns 504 at an angle to the weft yarns 504. Stated differently, the points where the loops 506 originate and return can be offset from each other along the x-axis (note Cartesian coordinate axes shown). The loops 506 can alternately extend in the positive x-direction and in the negative x-direction such that straight portions of the yarns 502A between loops 506 are offset from each other along the x-axis. This can provide certain advantages, such as preventing movement of or "locking" the warp yarns 502A relative to the weft yarns 504. Additionally, when the sealing member 500 is attached to a prosthetic valve with the warp yarns 502 extending axially in the direction of a longitudinal axis of the valve, the width W of the loops 506 can be oriented perpendicular, or substantially perpendicular, to the direction of blood flow through the valve such that the loops 506 present a relatively large flow obstruction. This can promote blood stasis and sealing around the prosthetic valve. The loop density (e.g., the number of loops per inch) of the pile can be varied by, for example, varying the length of the straight portions of the yarns 502A between the loops 506. Shortening the distance between loops 506 can increase the loop density of the pile, as shown in FIGS. 23 and 24, while increasing the distance between the loops 506 can decrease the loop density of the pile. The width of the loops 506 can be determined by, for example, the number of warp yarns over which the loops extend. For example, in FIG. 25 the loops extend over two warp yarns 502B such that the loops 506 of FIG. 25 are wider relative to the loops 506 of FIG. 22.

In certain embodiments, the loops 506 can be formed using warp-knitting techniques. In certain examples, the first warp yarns 502A can comprise 20 denier, 18 filament (20 d/18 f) and/or 30 d/18 f texturized yarns. The second warp yarns 502B can comprise 20 d/18 f yarns twisted with 12 twists per inch (tpi). In certain examples, the weft yarns 504 can be 20 d/18 f yarns with 12 tpi. The warp and weft yarns can be made from any of various biocompatible polymers, such as PET, UHMWPE, PTFE, etc. In other embodiments, the warp and/or weft yarns can have any selected denier and/or filament count, and can be made from any suitable natural or synthetic material.

Figures 26, 27, 28, 29:
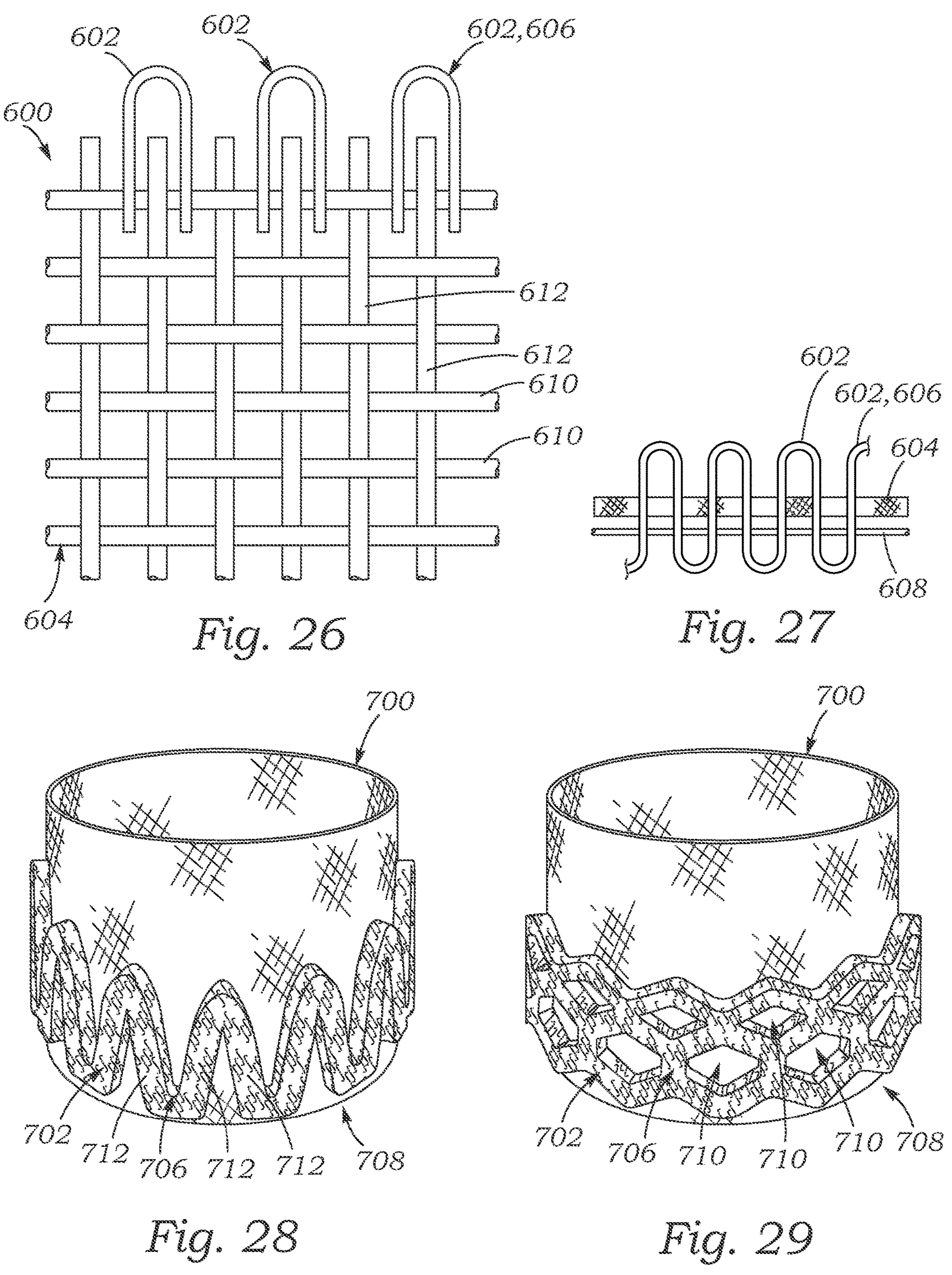
FIG. 26 is a perspective view of a portion of a sealing member including a plurality of loops embroidered into a base skirt fabric, according to one embodiment.
FIG. 27 is a cross-sectional side elevation view of the sealing member of FIG. 26.
FIGS. 28-30 are perspective views illustrating plush loop portions formed on sealing members in various patterns.

In some embodiments, loops may be formed on a prosthetic valve skirt by embroidery. In a representative embroidery technique, a yarn or thread is stitched to or through a base or foundation layer (e.g., a fabric), allowing a variety of shapes or patterns to be produced on the surface of the foundation layer. FIG. 26 illustrates a portion of a skirt 600 including a plurality of loops 602 embroidered into a base skirt fabric 604, according to one embodiment. The base skirt fabric can comprise a plurality of first yarns 610 interwoven with a plurality of second yarns 612 in, for example, a plain weave. Referring to FIG. 27, the loops 602 can be formed using a third yarn configured as an embroidery yarn 606, which may be a relatively high-density yarn or suture. In certain embodiments, in addition to the first or foundation layer 604, the skirt 600 may also optionally include a second layer configured as a locking layer 608. In particular embodiments, the locking layer 608 can comprise a relatively low-density, light, and/or thin yarn or suture that can be used to lock the embroidery yarn 606 on the back of the foundation layer 604.

Figures 30, 31:
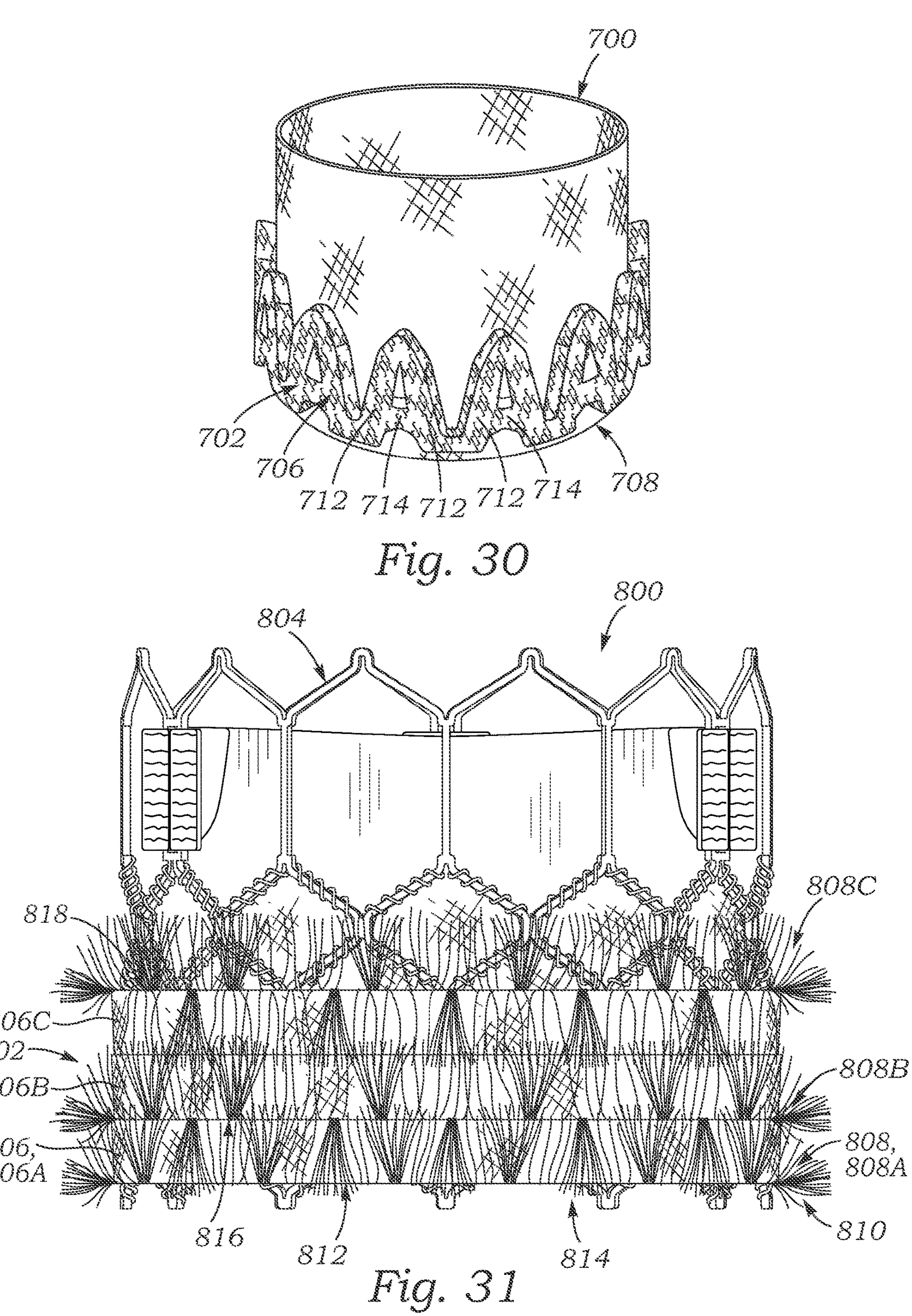
FIG. 31 is a side elevation view of a prosthetic heart valve including a sealing member comprising a plurality of woven fabric strips including fringed portions, according to another embodiment.

As noted above, loops may be embroidered on the surface of the prosthetic valve skirt having any specified location, length, width, spacing, shape, and/or pattern. FIGS. 28-30 illustrate just a few examples of the patterns that may be produced using the embroidery technique described above. For example, FIG. 28 illustrates a prosthetic valve skirt 700 including a plurality of loops generally indicated at 702 embroidered onto the skirt and forming a plush portion or pile 706. The plush portion 706 can include a plurality of angled portions 712 extending circumferentially around the skirt 700 in a zig-zag pattern from an end portion 708 (e.g., an inflow end portion) of the skirt to midway up the height of the skirt. FIG. 29 illustrates another variation of the plush portion 706 in which the plush portion defines cells 710. In certain embodiments, the cells 710 can correspond to openings or cells defined by the struts of the frame, such as the struts 26 of the prosthetic valve 10 of FIG. 1. In other embodiments, the cells of the plush portion 706 can correspond to the size and shape of the frame openings defined by the struts of the frame 202 of FIG. 9. FIG. 30 illustrates another variation of the plush portion 706 including straight portions 714 extending between adjacent angled portions 712. In certain embodiments, the loops 44 of FIG. 1 can be formed on the underlying fabric of the skirt 30 by embroidery.

FIG. 31 illustrates a prosthetic heart valve 800 including another embodiment of a sealing member or skirt 802 on a frame 804 configured as the frame of the Edwards Lifesciences Corporation SAPIEN® 3 prosthetic heart valve. The skirt 802 can comprise a plurality of woven portions configured as fabric strips 806 extending circumferentially around the frame. Each of the fabric strips 806 can comprise a corresponding fringe portion 808 comprising a plurality of filaments 810 extending radially outwardly at an angle from a circumferential edge portion (e.g., an inflow or outflow edge portion) of the fabric strip 806, similar to the skirt 100 of FIG. 7 above. In the illustrated embodiment, the skirt 802 can comprise three fabric strips 806A-806C having corresponding fringe portions 808A-808C. The fringe portion 808A of the fabric strip 806A can extend from an inflow edge 812 of the fabric strip 806A located proximate an inflow end 814 of the prosthetic valve. The filaments 810 of the fringe portion 808A can extend to about the second row II of strut members (see FIG. 12B). The filaments 810 of the second fabric strip 806B can extend from an inflow edge 816 of the fabric strip 806B, and can extend to about the level of the third row III of struts. The filaments 810 of the third fabric strip 806C can extend from an outflow edge 818 of the fabric strip 806C to about the level of the fourth row IV of struts.

The filaments 810 may comprise or originate from frayed yarns, textured yarns, etc. In certain embodiments, the fabric strips 806 of the sealing member 802 can comprise a yarn density of from 50 to 500 yarns per inch, 100 to 400 yarns per inch, 150 to 350 yarns per inch, or 150 to 300 yarns per inch. In certain embodiments, the fabric strips of the sealing member 802 can have a yarn density of 150 yarns per inch, or 300 yarns per inch. The yarns may have any suitable filament density, such as 5 to 100 filaments per yarn, 10 to 50 filaments per yarn, or 10 to 20 filaments per yarn. In particular embodiments, the yarns can comprise textured yarns having 18 filaments per yarn. The filaments may have thicknesses from 1 μm to 100 μm, 1 μm to 50 μm, or 1 μm to 20 μm. In particular embodiments, the filaments can have a thickness or diameter of 10 μm.

Figure 32:
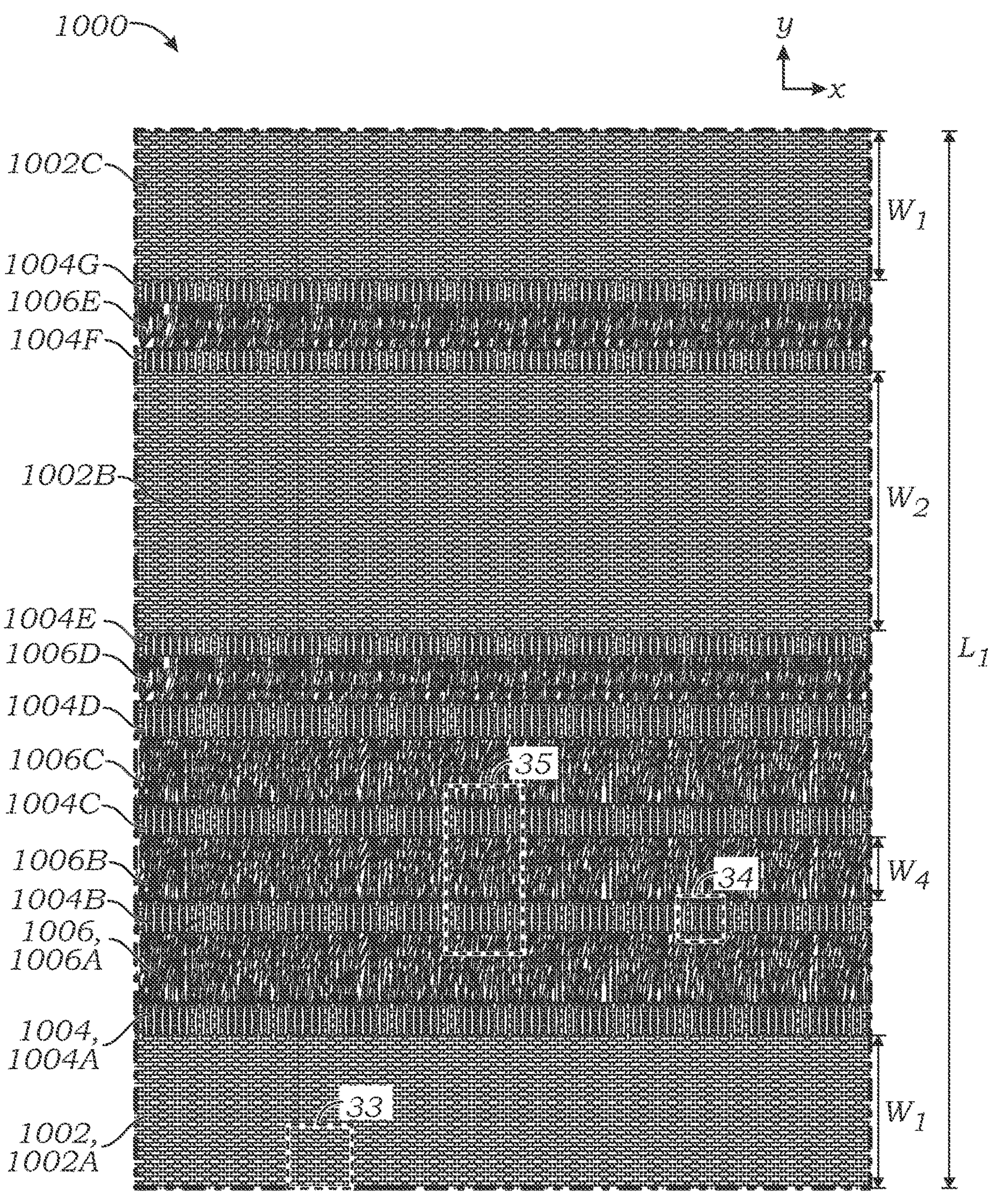
FIG. 32 is a plan view of a sealing member for a prosthetic heart valve including woven portions and floating yarn portions, according to another embodiment.

FIGS. 32-37 show a main cushioning layer, covering, or sealing member 1000, according to another embodiment. The sealing member 1000 can comprise a fabric body having a plurality of woven portions and a plurality of elastic, stretchable portions configured as floating yarn portions, and can be incorporated into any of the prosthetic valve outer coverings described herein. FIG. 32 illustrates the sealing member 1000 in a laid-flat configuration where the x-axis corresponds to the circumferential direction and the y-axis corresponds to the axial direction when the sealing member is attached to a frame of a prosthetic valve. The sealing member 1000 can comprise a plurality of first woven portions 1002 configured as woven strips or stripes extending along the x-axis, a plurality of second woven portions 1004 configured as woven strips or stripes extending along the x-axis, and a plurality of floating yarn portions, strips, or stripes 1006 extending along the x-axis. The various woven and floating yarn portions can be spaced apart from each other along the y-axis. In the illustrated configuration, the first woven portions 1002 can comprise a weave pattern that is different from the weave pattern of the second woven portions 1004, as described in greater detail below.

For example, in the illustrated configuration, the sealing member 1000 can comprise a first woven portion 1002A. Moving in a direction along the positive y-axis, the sealing member 1000 can further comprise a second woven portion 1004A, a floating yarn portion 1006A, a second woven portion 1004B, a floating yarn portion 1006B, a second woven portion 1004C, a floating yarn portion 1006C, a second woven portion 1004D, a floating yarn portion 1006D, a second woven portion 1004E, a first woven portion 1002B, a second woven portion 1004F, a floating yarn portion 1006E, a second woven portion 1004G, and a first woven portion 1002C at the opposite end of the sealing member from the first woven portion 1002A. In other words, the first woven portion 1002B and each of the floating yarn portions 1006A-1006E can be located between two second woven portions 1004 such that the first woven portion 1002B and each of the floating yarn portions 1006A-1006E are bounded or edged in a direction along the x-axis by respective second woven portions 1004.

Figures 33, 34:
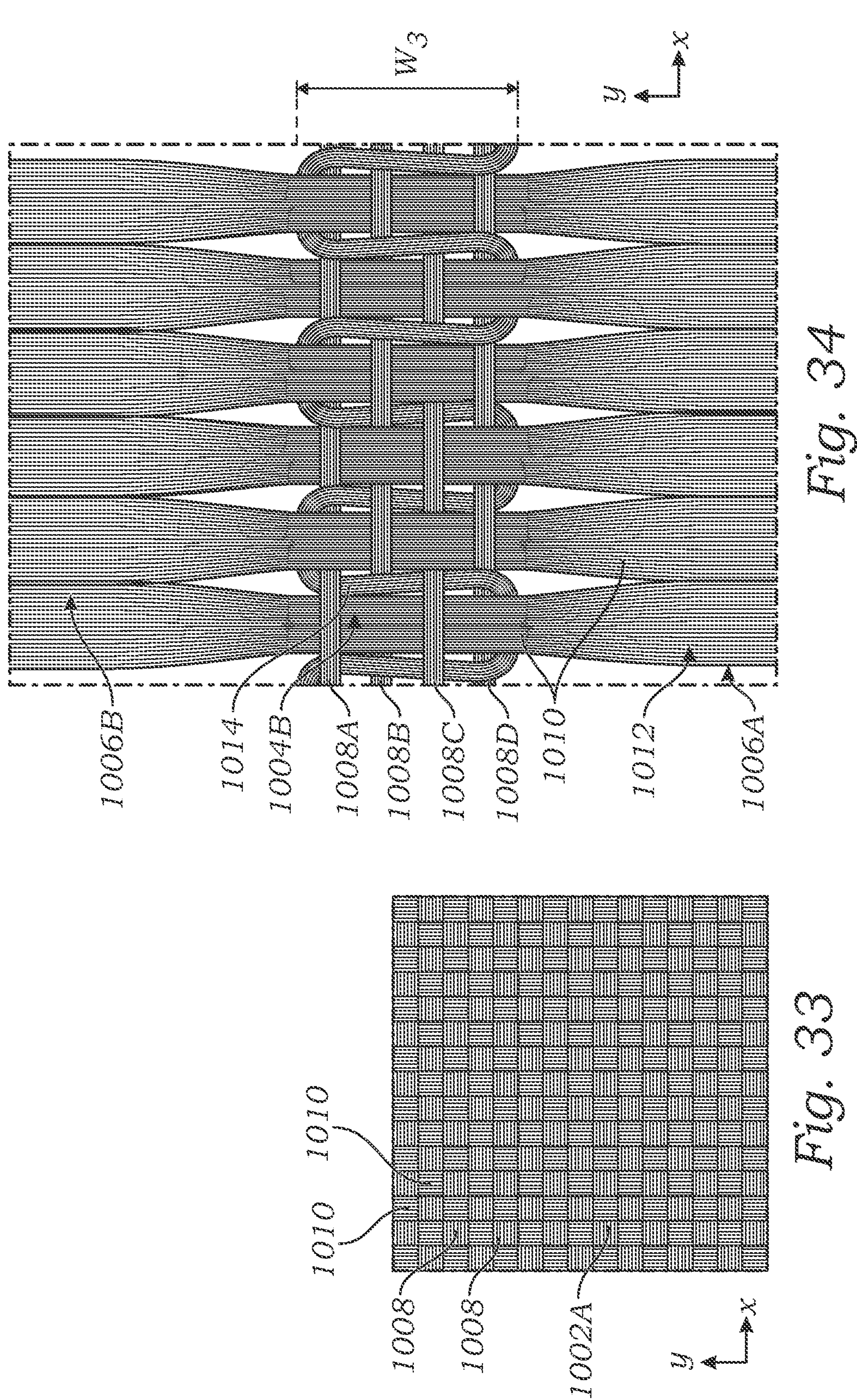
FIG. 33 is a magnified view of a first woven portion of the sealing member of FIG. 32.
FIG. 34 is a magnified view of a second woven portion of the sealing member of FIG. 32.

Referring to FIGS. 32 and 33, the sealing member 1000 can comprise a plurality of first yarns 1008 oriented generally along the x-axis and a plurality of second yarns 1010 oriented generally along the y-axis. In certain configurations, the first yarns 1008 can be warp yarns, meaning that during the weaving process the yarns 1008 are held by the loom, while the second yarns 1010 are weft yarns, which are interwoven with the warp yarns by a moving shuttle or weft-carrying mechanism during the weaving process. However, in other embodiments the first yarns 1008 may be weft yarns and the second yarns 1010 may be warp yarns.

Each of the first yarns 1008 and the second yarns 1010 can comprise a plurality of constituent filaments 1012 that are spun, wound, twisted, intermingled, interlaced, etc., together to form the respective yarns. Exemplary individual filaments 1012 of the second yarns 1010 can be seen in FIGS. 33-36. In some embodiments, the first yarns 1008 can have a denier of from about 1 D to about 200 D, about 10 D to about 100 D, about 10 D to about 80 D, about 10 D to about 60 D, or about 10 D to about 50 D. In some embodiments, the first yarns 1008 can have a filament count of 1 to about 600 filaments per yarn, about 10 to about 300 filaments per yarn, about 10 to about 100 filaments per yarn, about 10 to about 60 filaments per yarn, about 10 to about 50 filaments per yarn, or about 10 to about 30 filaments per yarn. In particular embodiments, the first yarns 1008 can have a denier of about 40 D and a filament count of 24 filaments per yarn. The first yarns 1008 may also be twisted yarns or non-twisted yarns. In the illustrated embodiment, the filaments 1012 of the first yarns 1008 are not texturized. However, in other embodiments, the first yarns 1008 may comprise texturized filaments.

The second yarns 1010 can be texturized yarns comprising a plurality of texturized filaments 1012. For example, the filaments 1012 of the second yarns 1010 can be texturized, for example, by twisting the filaments, heat-setting them, and untwisting the filaments as described above. In some embodiments, the second yarns 1010 can have a denier of from about 1 D to about 200 D, about 10 D to about 100 D, about 10 D to about 80 D, or about 10 D to about 70 D. In some embodiments, a filament count of the second yarns 1010 can be from 1 filament per yarn to about 100 filaments per yarn, about 10 to about 80 filaments per yarn, about 10 to about 60 filaments per yarn, or about 10 to about 50 filaments per yarn. In particular embodiments, the second yarns 1010 can have a denier of about 68 D and a filament count of about 36 filaments per yarn.

The first yarns 1008 and the second yarns 1010 can be woven together to form the woven portions of the sealing member, as noted above. For example, in the first woven portions 1002A-1002C, the first and second yarns 1008, 1010 can be woven together in a plain weave pattern in which the second yarns 1010 (e.g., the weft yarns) pass over a first yarn 1008 (e.g., a warp yarn) and then under the next first yarn in a repeating pattern. This weave pattern is illustrated in detail in FIG. 33. In some embodiments, the density of the first yarns 1008 can be from about 10 yarns per inch to about 200 yarns per inch, about 50 yarns per inch to about 200 yarns per inch, or about 100 yarns per inch to about 200 yarns per inch. In certain embodiments, the first woven portion 1002A and the first woven portion 1002C can be configured as selvedge portions, and can have a lower yarn density than the first woven portion 1002B to facilitate assembly on a valve frame. Other weave patterns may also be used, such as over two under two, over two under one, etc. The first woven portions may also be woven in plain weave derivative patterns such as twill, satin, or combinations of any of these.

In the second woven portions 1004A-1004G, the first and second yarns 1008, 1010 can be interwoven in another pattern that is different from the weave pattern of the first woven portions 1002A-1002C. For example, in the illustrated embodiment, the first and second yarns 1008, 1010 can be woven together in a leno weave pattern in the second woven portions 1004A-1004G. FIG. 34 illustrates the leno weave of the second woven portion 1004B in greater detail. With reference to FIG. 34, the leno weave can comprise one or more leno yarns or “leno ends” 1014, and four first yarns 1008A, 1008B, 1008C, and 1008D, also referred to as “warp ends.” The pattern illustrated in FIG. 34 includes a single leno yarn 1014 in the manner of a half-leno weave. However, in other embodiments, the leno weave pattern may be a full-leno weave comprising two intertwining leno yarns 1014, or other leno-derived weaves. Examples of various leno weaves and associated weaving techniques are illustrated in FIGS. 39A-39J.

In the half-leno weave illustrated in FIG. 34, the first yarns 1008A-1008D can extend parallel to the x-axis, and the second yarns 1010 can be interwoven with the first yarns 1008A-1008D in, for example, a plain weave. The leno yarn 1014 can weave around the first yarns 1008A-1008D such that the leno yarn 1014 crosses over, or on top of, the first yarns 1008A-1008D with each pass in the positive y-direction, crosses beneath or behind the next second yarn 1010 in the x-direction, and extends back over the first yarns 1008A-1008D in the negative y-direction. This pattern can be repeated along the length of the second woven portion 1004B. In this manner, the second woven portions 1004 can be relatively narrow, strong woven portions spaced axially from each other along the frame when the sealing element is mounted to a frame. The leno yarn 1014 can serve to keep the first yarns 1008A-1008D and the second yarns 1010 in place with respect to each other as the prosthetic valve is crimped and expanded, and can impart strength to the second woven portions 1004 while minimizing width.

In certain embodiments, each of the second woven portions 1004A-1004G can comprise the leno weave pattern described above. In other embodiments, one or more of the second woven portions 1004A-1004G may be configured differently, such as by incorporating more or fewer first yarns 1008 in the leno weave, having multiple leno ends woven around multiple groupings of yarns 1008, etc. In yet other embodiments, a chemical locking method can be used where the leno weave and/or a plain weave includes warp yarns having core-sheath construction filaments. The sheath of the individual filaments can be made of low-melt temperature polymers such as biocompatible polypropylene, and the core of the filaments be made of another biocompatible polymer such as polyester. After the weaving process, the heat setting process described below can enable the softening and/or melting of the sheath. Upon cooling, the softened sheath polymer can bond the core polyester filaments together. This can create a bonded body enabling locking of the woven structure.

Referring again to FIG. 32, the floating yarn portions 1006 can comprise yarns extending in only one axis between respective second woven portions 1004 that are spaced apart from each other along the y-axis. For example, taking the floating yarn portion 1006A as a representative example, the floating yarn portion 1006A can comprise a plurality of second yarns 1010 that exit the leno weave of the second woven portion 1004A, extend across the floating yarn portion 1006A, and are incorporated into the leno weave of the second woven portion 1004B. In some embodiments, the density of the second yarns in the floating yarn portions 1006 can be from about 10 to about 200 yarns per inch, about 50 to about 200 yarns per inch, or about 100 to about 200 yarns per inch. In particular embodiments, the density of the second yarns 1010 can be about 60-80 yarns per inch. In other embodiments, the floating yarn portions can include first yarns 1008 disposed under or over, but not interwoven with, the second yarns 1010 such that the second yarns float over the first yarns or vice versa. In yet other embodiments, the floating yarn portions may instead be configured as any other elastically stretchable structure, such as elastically stretchable woven, knitted, braided, or non-woven fabrics, or polymeric membranes, to name a few, that is elastically stretchable at least in the axial direction of the prosthetic valve.

In the illustrated embodiment, each of the woven portions 1002A-1002C and 1004A-1004G, and each of the floating yarn portions 1006A-1006E can have width dimensions in the y-axis direction. The widths of the constituent portions can be configured such that the overall length $L_1$ (FIG. 32) of the sealing member 1000 generally corresponds to the axial length of a prosthetic heart valve in the expanded configuration. For example, in the illustrated embodiment the first woven portions 1002A and 1002C can each have a width $W_1$. In certain embodiments, the width $W_1$ can be configured such that portions of the first woven portions 1002A and 1002C can be folded over the inflow and outflow ends of the frame of a prosthetic valve.

The first woven portion 1002B can have a width $W_2$. With reference to FIG. 12B, when the sealing member 1000 is used in combination with the frame of the Edwards Lifesciences SAPIEN® 3 prosthetic heart valve, the width $W_2$ can be configured to correspond to the axial dimension of the frame openings defined by the strut members between the fourth row IV and the fifth row V of struts. In some embodiments, the width $W_2$ of the first woven portion 1002B can be about 2 mm to about 20 mm, about 2 mm to about 12 mm, or about 3 mm to about 10. In particular embodiments, the width $W_2$ can be about 7 mm.

The second woven portions 1004A-1004G can have widths $W_3$ (FIG. 34). In the illustrated embodiment, all of the second woven portions 1004A-1004G have the width $W_3$, but one or more of the second woven portions may also have different widths. In certain embodiments, the width $W_3$ can be relatively short, such as about 0.1 mm to about 3 mm, about 0.1 mm to about 2 mm, or about 0.1 mm to about 1 mm. In particular embodiments, the width $W_3$ can be about 1 mm.

Figures 35, 36:
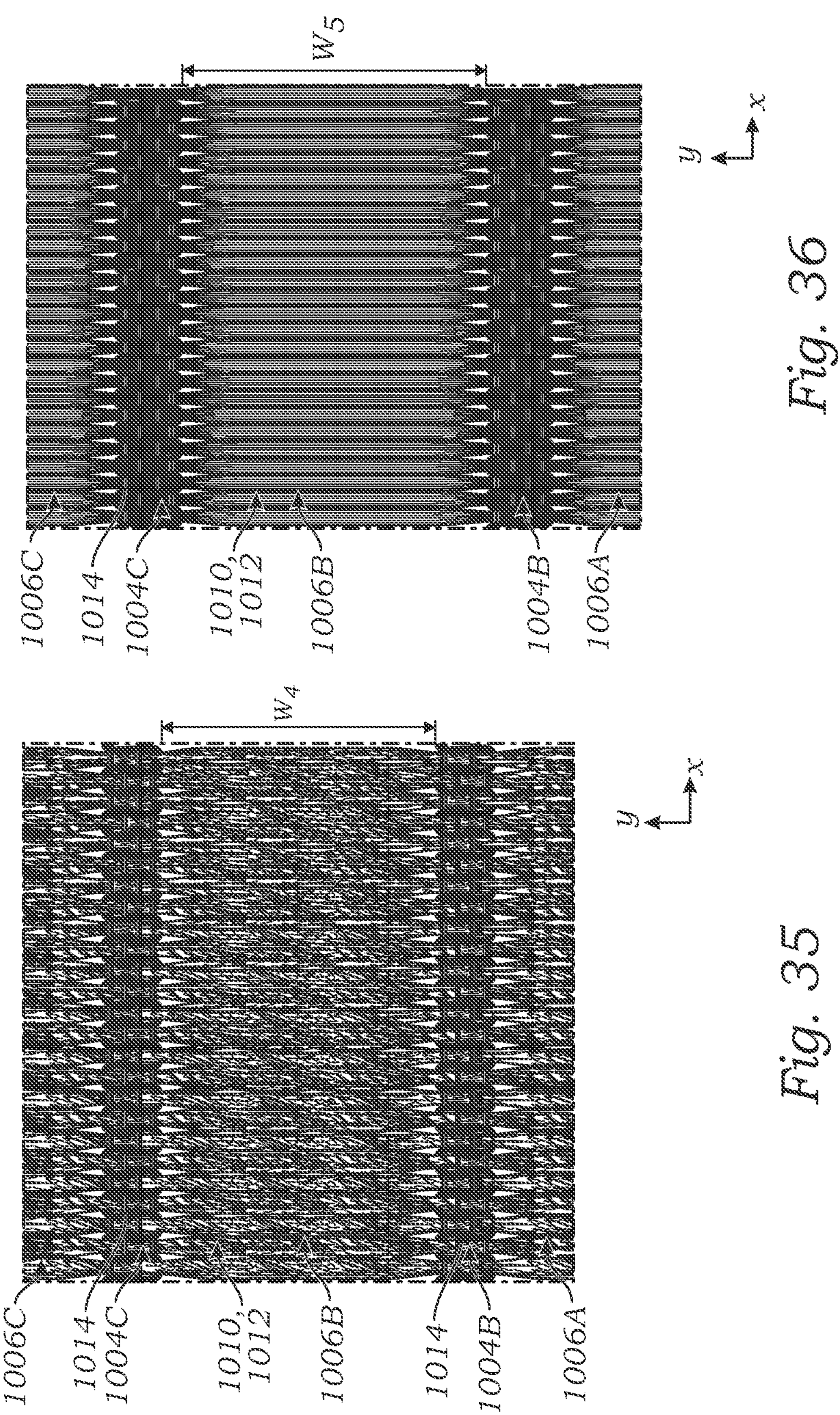
FIG. 35 is a magnified view of a floating yarn portion of the sealing member of FIG. 32 in a relaxed state.
FIG. 36 illustrates the floating yarn portion of FIG. 35 in a stretched state.

With reference to FIGS. 32 and 35-38, in certain embodiments the sealing member 1000, and in particular the floating yarn portions 1006A-1006E, can be resiliently stretchable between a first, natural, or relaxed configuration (FIGS. 32 and FIG. 35) corresponding to the radially expanded state of the prosthetic valve, and a second, elongated, or tensioned configuration (FIGS. 37 and 38) corresponding to the radially compressed state of the prosthetic valve. Thus, the floating yarn portions 1006A-1006E can have initial widths $W_4$ when the sealing member 1000 is in the relaxed, unstretched state. FIG. 35 illustrates a portion of the floating yarn portion 1006B in the natural, relaxed state. When the fabric is in the relaxed state, the textured filaments 1012 of the second yarns 1010 can be kinked and twisted in many directions such that the floating yarn portion 1006B has a bulky, billowy, or pillow-like quality. When tensioned, the kinks, twists, etc., of the filaments 1012 can be pulled at least partially straight along the y-axis, causing the second yarns 1010 to elongate. With reference to FIG. 36, the width of the floating yarn portions 1006 can thus increase to a second width $W_5$ that is larger than the initial width $W_4$.

Figure 37:
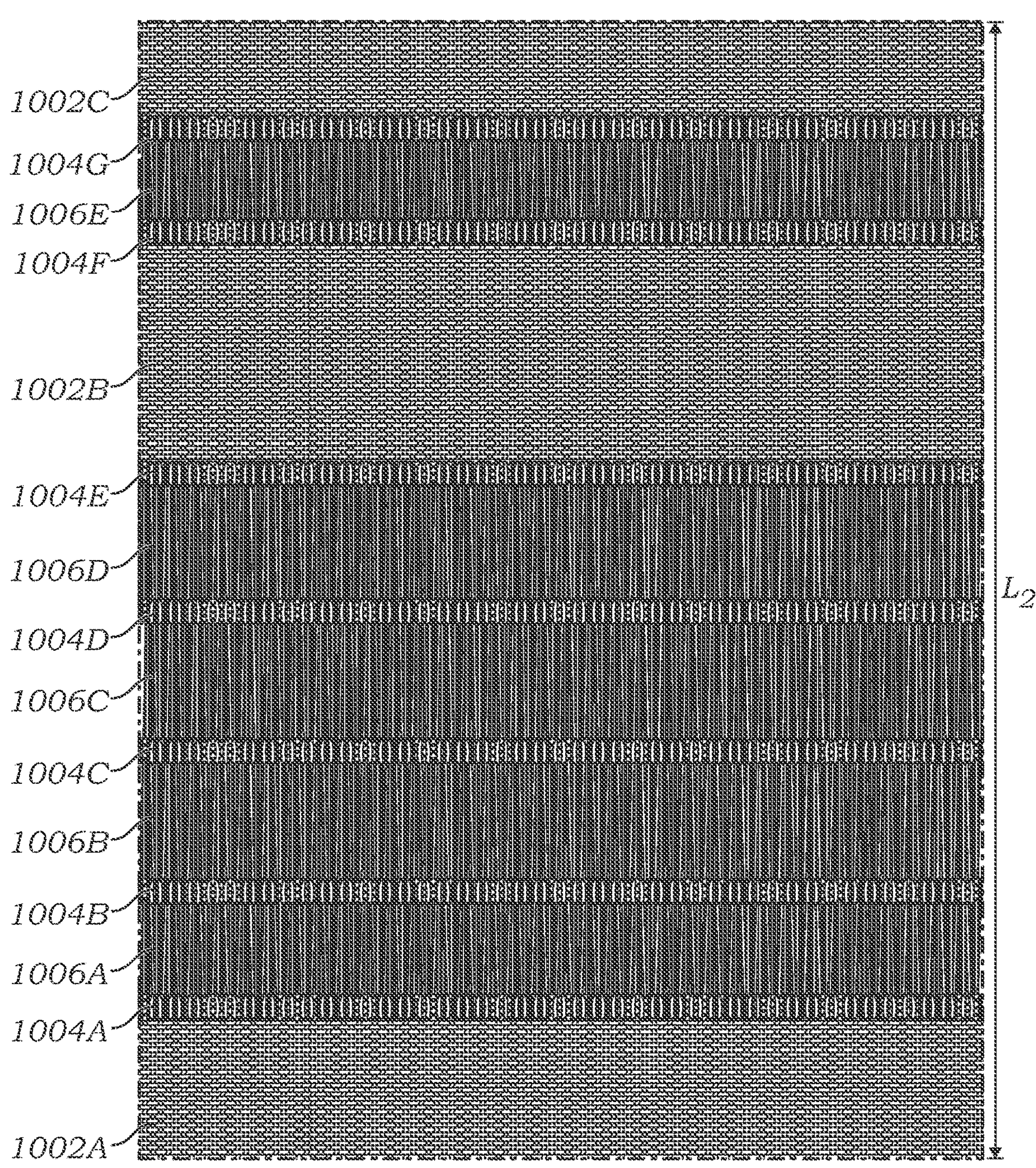
FIG. 37 is a plan view of the sealing member of FIG. 32 in a stretched state.

The cumulative effect of the floating yarn portions 1006A-1006E increasing in width from the initial width $W_4$ to the second width $W_5$ is that the overall axial dimension of the sealing member 1000 can increase from the initial length $L_1$ (FIG. 32) to a second overall length $L_2$ (FIG. 37) that is greater than the first length $L_1$. FIG. 37 illustrates the sealing member 1000 in the stretched configuration with the second yarns 1010 of the floating yarn portions 1006A-1006E straightened under tension such that the overall length of the sealing member increases to the second length $L_2$. In certain embodiments, the size, number, spacing, etc., of the floating yarn portions 1006, and the degree of texturing of the constituent second yarns 1010, can be selected such that the second length $L_2$ of the sealing member 1000 corresponds to the length of a frame of a prosthetic valve when the prosthetic valve is crimped for delivery on a delivery apparatus. In particular embodiments, the relaxed initial width $W_4$ of the floating yarn portions 1006 can be about 1 mm to about 10 mm, about 1 mm to about 8 mm, or about 1 mm to about 5 mm. In particular embodiments, the initial width $W_4$ can be about 4 mm.

FIG. 38 illustrates an edge portion of the sealing member 1000 gripped between a pair of grippers 1050. In certain embodiments the bulky, billowy nature of the texturized yarns 1010 in the floating yarn portions 1006 can result in the floating yarn portions 1006 having a thickness $t_1$ that is greater than a thickness $t_2$ of the woven portions 1002 and 1004. For example, in certain embodiments the thickness $t_1$ of the floating yarn portions 1006 can be two times, three times, four times, five times, six times, or even ten times greater than the thickness $t_2$ of the woven portions 1002 and 1004, or more, when the sealing member is in the relaxed state. This can allow the floating yarn portions 1006 to cushion the native leaflets between the valve body and/or against an anchor or ring into which the prosthetic valve is implanted. The floating yarn portions 1006 can also occupy voids or space in the anatomy, and/or promote tissue growth into the floating yarn portions, as in the embodiments described above. When tension is applied to stretch the floating yarn portions 1006, the thickness $t_1$ can decrease as the texturized second yarns 1010 straighten. In certain embodiments, the thickness $t_1$ can be equal or nearly equal to the thickness $t_2$ of the woven portions 1002 and 1004 when the sealing member is in the tensioned state. When the tension on the sealing member 1000 is released, such as during expansion of the prosthetic valve, the yarns 1012 can resume their texturized shape and the thickness of the floating yarn portions 1006 can return to the initial thickness $t_1$.

In certain embodiments, the floating yarn portions 1006A-1006E can be configured such that the sealing member 1000 can elongate by about 10% to about 500%, about 10% to about 300%, about 10% to about 200%, about 10% to about 100%, about 10% to about 80%, or about 10% to about 50%. In particular embodiments, the floating yarn portions 1006A-1006E can be configured to allow the sealing member 1000 to elongate by about 30%, corresponding to the elongation of the frame 1022 between the expanded and crimped configurations. As noted above, the increase in width of the floating yarn portions 1006A-1006E can also result in a corresponding decrease in thickness of the floating yarn portions, reducing the crimp profile of the prosthetic valve during delivery.

In some embodiments, the first and second yarns 1008 and 1010 can comprise any of various biocompatible thermoplastic polymers such as PET, Nylon, ePTFE, UHMWPE, etc., or other suitable natural or synthetic fibers. In certain embodiments, the sealing member 1000 can be woven on a loom, and can then be heat-treated or heat-set to achieve the desired size and configuration. For example, depending upon the material selected, heat-setting can cause the sealing member 1000 to shrink. Heat-setting can also cause a texturizing effect, or increase the amount of texturizing, of the second yarns 1010. After heat treatment, the openings 1016 can be created in the first woven portion 1002B (e.g., by laser cutting), and the sealing member can be incorporated into an outer covering such as the covering 1018 for assembly onto a prosthetic valve. In some embodiments, the openings 1016 can also be created before heat treatment.

The loops, filaments, floating portions, etc., of the prosthetic sealing members described herein can be configured to promote a biological response in order to form a seal between the prosthetic valve and the surrounding anatomy, as described above. In certain configurations, the sealing elements described herein can be configured to form a seal over a selected period of time. For example, in certain embodiments, the open, porous nature of the loops, filaments, yarns, etc., can allow a selected amount of paravalvular leakage around the prosthetic valve in the time period following implantation. The amount paravalvular leakage past the seal structure may be gradually reduced over a selected period of time as the biological response to the loops, filaments, yarns, etc., causes blood clotting, thrombus formation, etc. In some embodiments, the sealing members, and in particular the loops, filaments, yarns, etc., of the paravalvular sealing structure, may be treated with one or more agents that inhibit the biological response to the sealing structures. For example, in certain embodiments, the loops, filaments, yarns, etc., may be treated with heparin. In certain embodiments, the amount or concentration of the agent(s) may be selected such that the agents are depleted after a selected period of time (e.g., days, weeks, or months) after valve implantation. As the agent(s) are depleted, the biological response to the loops, filaments, yarns, etc., of the sealing structures may increase such that a paravalvular seal forms gradually over a selected period of time. This may be advantageous in patients suffering from left atrial remodeling (e.g., due to mitral regurgitation), by providing an opportunity for the remodeling to reverse as regurgitation past the prosthetic valve is gradually reduced.

Figures 39C, 39D, 39E, 39F, 39G, 39H, 39I, 39J:
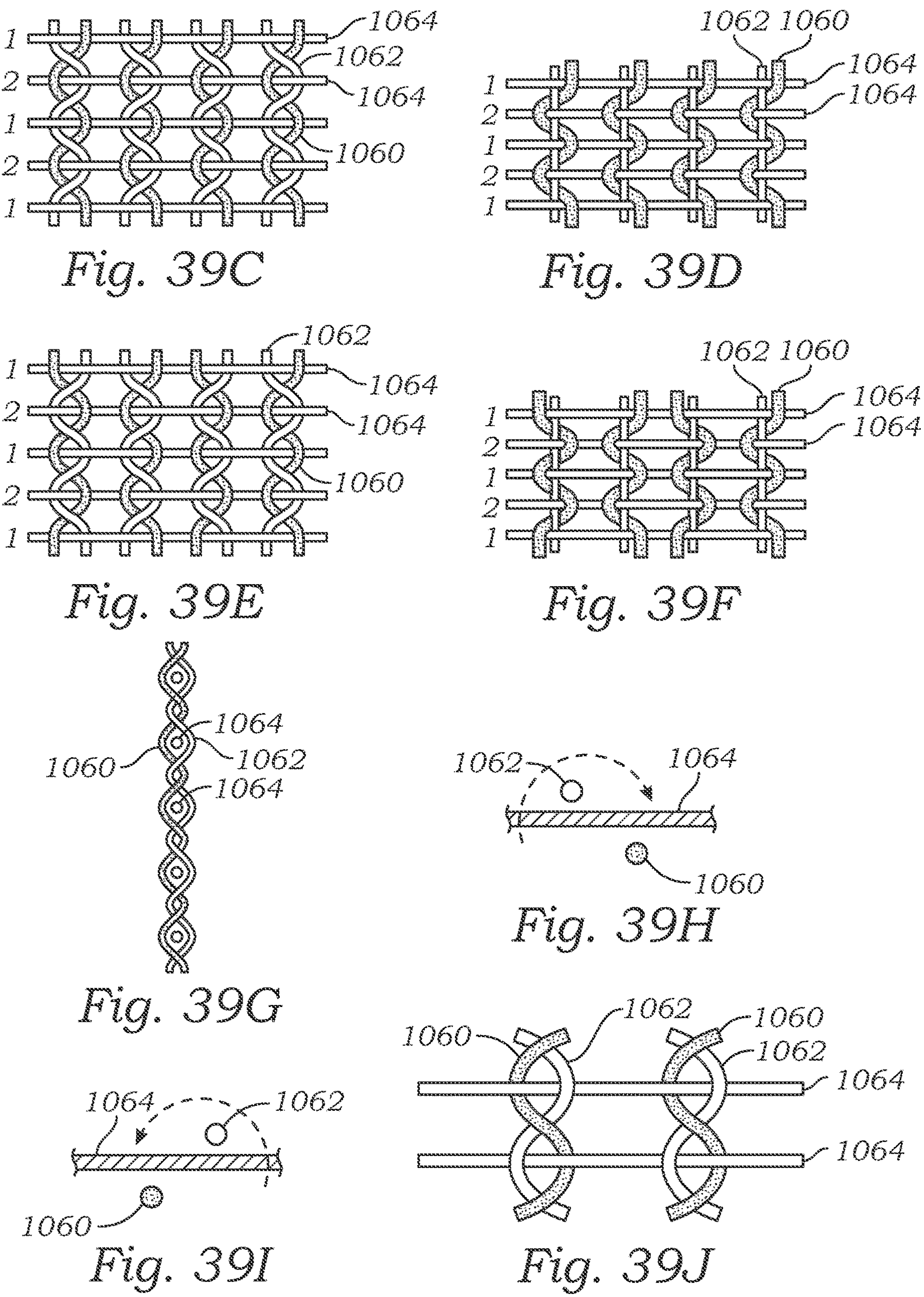

FIGS. 39A-39J illustrate various leno weaves and leno weaving techniques that may be used to produce the sealing member 1000, or any of the other sealing members described herein. FIG. 39A is a cross-sectional view illustrating a shed (e.g., the temporary separation of warp yarns to form upper and lower warp yarns) in which a leno yarn, "leno end," or "crossing end" 1060 forms the top shed on the left of the figure above a weft yarn 1064 and a standard warp yarn 1062 forms the bottom shed. FIG. 39B illustrates a successive shed in which the leno yarn 1060 forms the top shed on the right of the standard warp yarn 1062. In FIGS. 39A and 39B, the leno yarn 1060 may cross under the standard yarn 1062 in a pattern known as bottom douping. Alternatively, the leno yarn 1060 may cross over the standard yarn 1062, known as top douping, as in FIGS. 39H and 39I.

FIG. 39C illustrates a leno weave interlacing pattern produced when one warp beam is used on a loom, and the distortion or tension of the leno yarns 1060 and the standard yarns 1062 is equal such that both the yarns 1060 and the yarns 1062 curve around the weft yarns 1064. FIG. 39D illustrates a leno weave lacing pattern produced when multiple warp beams are used, and the leno yarns 1060 are less tensioned than the standard yarns 1062 such that the standard yarns 1062 remain relatively straight in the weave, and perpendicular to the weft yarns 1064, while the leno yarns 1060 curve around the standard yarns 1062.

FIG. 39E illustrates an interlacing pattern corresponding to FIG. 39C, but in which alternate leno yarns 1060 are point-drafted (e.g., a technique in which the leno yarns are drawn through heddles) such that adjacent leno yarns 1060 have opposite lacing directions. FIG. 39F illustrates an interlacing pattern corresponding to FIG. 39D, but in which the leno yarns 1060 are point-drafted such that adjacent leno yarns have opposite lacing directions.

FIG. 39G is a cross-sectional view of a plain leno weave structure taken through the weft yarns 1064.

FIG. 39J illustrates a representative leno weave as viewed from the reverse side of the fabric.

Example 1

In a first representative example, an acute animal trial was conducted in which prosthetic heart valves including various skirts of the type shown in FIG. 31 were implanted in the aortic valves of sheep. A first prosthetic valve that was tested included a sealing member or skirt with a yarn density of 300 yarns per inch, in which the yarns had a fringe or filament density of 18 filaments per yarn. A second prosthetic valve had a skirt with a yarn density of 150 yarns per inch, in which the yarns had a filament density of 18 filaments per yarn. A prosthetic valve having no exterior skirt was also implanted as a control.

Prior to implantation, the prosthetic valves were partially crimped, and a stack of annuloplasty rings (e.g., two concentrically stacked annuloplasty rings) were attached around the exterior of the prosthetic valves by suturing. Each stack of annuloplasty rings had a plastic cable tie cinched around the bodies of the annuloplasty rings. The stacks of annuloplasty rings were attached to the prosthetic valves such that the heads of the cable ties were located between the outer skirt of the prosthetic valve and the bodies of the annuloplasty rings. In other words, the heads of the cable ties served to space the bodies of the annuloplasty rings away from the prosthetic valves such that an axially-extending channel was defined between the outer skirt and the annuloplasty rings on both sides of the cable tie head in order to induce paravalvular leakage past the prosthetic valves. For the control prosthetic valve without an exterior skirt, the head of the cable tie spaced the annuloplasty rings away from the exterior surface of the prosthetic valve frame.

The prosthetic valves were implanted in a surgical procedure. A baseline amount of paravalvular leakage through the space between the prosthetic valve frame and the stack of annuloplasty rings was determined using echocardiography and/or angiography while the patient was heparinized. Heparinization was then reversed (e.g., by administration of protamine sulfate), and paravalvular leakage was then assessed using echocardiography and angiography over a period of 5 to 30 minutes. The prosthetic valves were then surgically retrieved.

For the first prosthetic valve having the skirt with the yarn density of 300 yarns per inch, no paravalvular leakage was observed before or after heparin reversal. Upon explant, the space between the outer skirt and the attached annuloplasty rings had become completely sealed by thrombus formation, and the head of the cable tie had become at least partially encapsulated by one or more thrombi.

For the second prosthetic valve having the skirt with the yarn density of 150 yarns per inch, paravalvular leakage having an angiographic grade of 2+ was observed by echocardiography, and a grade of 1+ by angiography, before heparin reversal. As used herein, reference to "paravalvular leakage" or "regurgitation" graded at, e.g., 1+, 2+, 3+, or 4+ refers to the angiographic grading guidelines provided by the American Society of Echocardiography using assessment techniques including, for example, echocardiography, angiography, color flow Doppler, fluoroscopy, etc. (Zoghbi et al., ASE Guidelines and Standards: Recommendations for Noninvasive Evaluation of Native Valvular Regurgitation—A Report from the American Society of Echocardiography Developed in Collaboration with the Society for Cardiovascular Magnetic Resonance, Journal of the American Society of Echocardiography, April 2017). After heparin reversal, no paravalvular leakage was detected by either echocardiography or angiography. Upon explant, the space between the outer skirt and the attached annuloplasty rings had become completely sealed by thrombus formation, and the head of the cable tie had become at least partially encapsulated by one or more thrombi.

For both the first and second prosthetic valves including fringed skirts, the immediate acute reduction in paravalvular leakage may be attributable to interaction between blood and the yarn filaments. The continued gradual reduction in paravalvular leakage observed for the second prosthetic valve post-heparin reversal may be attributable to a continued cellular-level biological response resulting in thrombus formation and sealing. For the first prosthetic valve with the yarn density of 300 yarns per inch, the sealing of the space between the frame and the annuloplasty rings occurred nearly immediately. For the second prosthetic valve with the yarn density of 150 yarns per inch, the time to full closure or sealing of the space between the frame and the annuloplasty rings (e.g., no detectable paravalvular leakage) was 5 to 30 minutes.

For the control prosthetic valve that had no outer skirt, paravalvular leakage having a grade of 2+ or greater was observed under heparinization. After heparin reversal, paravalvular leakage having an angiographic grade of 2+ to 3+ was observed. Upon explant, the space between the annuloplasty rings and the frame of the prosthetic valve was fully open or patent, and no appreciable biological sealing had occurred.

General Considerations

Any of the sealing element embodiments disclosed herein can be used in combination with any of the disclosed prosthetic heart valve and/or frame embodiments. A prosthetic heart valve can also include any of the sealing elements described herein, or portions thereof, in any combination.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In the context of the present application, the terms "lower" and "upper" are used interchangeably with the terms "inflow" and "outflow", respectively. Thus, for example, in certain configurations the lower end of the valve is its inflow end and the upper end of the valve is its outflow end.

As used herein, the term "proximal" refers to a position, direction, or portion of a device that is closer to the user and further away from the implantation site. As used herein, the term "distal" refers to a position, direction, or portion of a device that is further away from the user and closer to the implantation site. Thus, for example, proximal motion of a device is motion of the device toward the user, while distal motion of the device is motion of the device away from the user. The terms "longitudinal" and "axial" refer to an axis extending in the proximal and distal directions, unless otherwise expressly defined.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

In view of the many possible embodiments to which the principles of the disclosed technology may be applied, it should be recognized that the illustrated embodiments are only preferred examples and should not be taken as limiting the scope of the disclosure. Rather, the scope of the disclosure is at least as broad as the following claims.

The invention claimed is:

1. A prosthetic heart valve, comprising:
   an annular frame having an inflow end and an outflow end;
   a leaflet structure positioned within an interior of the frame; and
   an outer skirt positioned on an exterior of the frame, wherein the outer skirt comprises a hydrophilic surface treatment;
   wherein the outer skirt comprises a plurality of portions comprising a plurality of filaments extending outwardly from an outer surface of the outer skirt;
   wherein the outer skirt comprises a plurality of strips that lack filaments extending outwardly from the outer surface, wherein the strips that lack filaments are in an alternating arrangement with the portions comprising outwardly extending filaments; and
   wherein the portions comprising outwardly extending filaments are spaced apart from each other by the plurality of strips that lack outwardly extending filaments.

2. The prosthetic heart valve of claim 1, wherein the outer skirt comprises a plurality of filaments, wherein at least some of the plurality of filaments are coated with a hydrophilic substance to form the hydrophilic surface treatment.

3. The prosthetic heart valve of claim 2, wherein the hydrophilic surface treatment is covalently bonded to fibers of the coated filaments.

4. The prosthetic heart valve of claim 2, wherein end portions of selected ones of the plurality of filaments extend from an edge of the outer skirt to form a fringe portion extending outwardly from an outer surface of the outer skirt.

5. The prosthetic heart valve of claim 4, wherein filaments of the plurality of filaments of the fringe portion comprise a plurality of fibers.

6. The prosthetic heart valve of claim 1, wherein the hydrophilic surface treatment comprises a polyethylene glycol (PEG) coating.

7. The prosthetic heart valve of claim 1, wherein the hydrophilic surface treatment is on an exterior surface of the outer skirt.

8. The prosthetic heart valve of claim 1, wherein the outer skirt comprises a polymeric film.

9. The prosthetic heart valve of claim 1, wherein the hydrophilic surface treatment comprises a lubricious coating.

10. The prosthetic heart valve of claim 1, wherein the prosthetic heart valve is radially expandable and compressible, and wherein, when in a radially compressed state, the prosthetic heart valve is sized and shaped to be disposed within a sheath of a delivery apparatus for transcatheter delivery of the prosthetic heart valve in the radially compressed state.

11. The prosthetic heart valve of claim 10, wherein the prosthetic heart valve is sized and shaped for advancement of the prosthetic heart valve from the sheath of the delivery apparatus for deployment of the prosthetic heart valve at a delivery site.

12. A prosthetic heart valve delivery system comprising:
   the prosthetic heart valve of claim 1; and
   a delivery apparatus comprising:
      a shaft; and
      a sheath disposed at the end of the shaft, the sheath sized and shaped to receive therein the prosthetic heart valve in a radially compressed state.

13. A prosthetic heart valve, comprising:
   an annular frame having an inflow end and an outflow end;
   a leaflet structure positioned within an interior of the frame; and
   an outer skirt positioned on an exterior of the frame, wherein the outer skirt comprises a polymeric film, a hydrophilic coating, a plurality of portions comprising outwardly extending fibers that extend outwardly relative to an outer surface of the polymeric film, wherein the portions comprising outwardly extending fibers are spaced apart from each other by a plurality of strips that lack outwardly extending fibers, wherein the strips that lack outwardly extending fibers are in an alternating arrangement with the portions that comprise outwardly extending fibers.

14. The prosthetic heart valve of claim 13, wherein the hydrophilic coating comprises a polyethylene glycol (PEG) coating.

15. The prosthetic heart valve of claim 13, wherein the hydrophilic coating comprises a lubricious coating.

16. A prosthetic heart valve delivery system comprising:
   the prosthetic heart valve of claim 13; and
   a delivery apparatus comprising:
      a shaft; and
      a sheath disposed at the end of the shaft, the sheath sized and shaped to receive therein the prosthetic valve in a radially compressed state.

17. A prosthetic heart valve, comprising:
   an annular frame having an inflow end and an outflow end;
   a leaflet structure positioned within an interior of the frame; and
   an outer skirt positioned on an exterior of the frame, wherein the outer skirt comprises a polymeric film, a plurality of outwardly extending fibers that extend outwardly relative to the exterior surface of the film, and a polyethylene glycol (PEG) coating covalently bonded on the exterior surface of the outer skirt, wherein the PEG coating forms a lubricious surface on the exterior surface of the outer skirt.

18. The prosthetic heart valve of claim 17, wherein the polyethylene glycol (PEG) coating is covalently bonded to the plurality of fibers.

* * * * *